US006440445B1

(12) United States Patent
Nowak et al.

(10) Patent No.: US 6,440,445 B1
(45) Date of Patent: Aug. 27, 2002

(54) METHODS AND COMPOUNDS FOR TREATMENT OF ABNORMAL UTERINE BLEEDING

(75) Inventors: Romana A. Nowak, West Roxbury; Elizabeth A. Stewart, Cambridge, both of MA (US)

(73) Assignee: Brigham & Women's Hospital, Boston, MA (US)

( * ) Notice: Subject to any disclaimer, the term of this patent is extended or adjusted under 35 U.S.C. 154(b) by 0 days.

(21) Appl. No.: 09/011,969

(22) PCT Filed: Sep. 30, 1997

(86) PCT No.: PCT/US97/17998

§ 371 (c)(1), (2), (4) Date: Feb. 20, 1998

(87) PCT Pub. No.: WO98/14169

PCT Pub. Date: Apr. 9, 1998

Related U.S. Application Data

(60) Provisional application No. 60/027,082, filed on Sep. 30, 1996, and provisional application No. 60/027,406, filed on Sep. 30, 1996.

(51) Int. Cl.$^7$ ................................................ A61F 2/02

(52) U.S. Cl. ...................................... 424/423; 424/426

(58) Field of Search ............................... 424/423, 426

(56) References Cited

U.S. PATENT DOCUMENTS

| | | |
|---|---|---|
| 3,851,648 A | 12/1974 | Brooke |
| 4,882,318 A | 11/1989 | Vlodavsky et al. |
| 5,225,420 A | 7/1993 | Cazenave et al. |
| 5,449,678 A | 9/1995 | Pines et al. |
| 5,852,024 A | 12/1998 | Pines et al. |
| 6,017,949 A * | 1/2000 | D'Amato et al. ........... 514/450 |

FOREIGN PATENT DOCUMENTS

| | | |
|---|---|---|
| WO | WO 95/24907 | 9/1995 |
| WO | WO 96/19224 | 6/1996 |

(List continued on next page.)

OTHER PUBLICATIONS

Stewart et al, Leiomyoma–related bleeding: a classic hypothesis updated for the molecular era. Human reproductive Update, vol. 2, No. 4, pp. 295–305, Jul. 1996.*

(List continued on next page.)

*Primary Examiner*—Carlos Azpuru
(74) *Attorney, Agent, or Firm*—David J. Powsner; Nutter McClennen & Fish LLP.

(57) ABSTRACT

The invention provides methods for treating abnormal uterine bleeding via application of compounds that block uterine stromal cell response to angiogenic growth factors by interfering with the growth factors themselves, by blocking receptors in the uterine epithelial or stromal cells to those growth factors, and/or by inhibiting other receptors to those growth factors. The compounds include interferons, particularly type I interferons, pirfenidone, heparin, heparin-like polyaromatic anionic compounds, heparin-sulfate-based compounds, secreted or soluble FGF receptors, and/or RGD-peptide. The angiogenic growth factors to which response is blocked include basic fibroblast growth factor (bFGF), FGF receptors (FGFR), acidic fibroblast growth factor (aFGF), transforming growth factor β (TGF-β), platelet-derived growth factor (PDGF), heparin binding epidermal growth factor (HBEGF), vascular endothelial growth factor (VEGF), parathyroid hormone-related protein (PTHrP) and/or prolactin. The methods contemplate introducing the aforementioned response-blocking compounds into the body of a patient either systemically, e.g., via injection or implant, or locally to the uterus, e.g., via medicated intrauterine devices, foams and the like. The invention also provides methods for female contraception comprising administering the aforementioned response-blocking compounds, along with progestin or a progestin-only contraceptive, to inhibit pregancy while reducing bleeding otherwise associated with such contraceptives.

46 Claims, 21 Drawing Sheets-

Day of Menstrual Cycle

FOREIGN PATENT DOCUMENTS

| WO | WO 97/06805 | 2/1997 |
|---|---|---|
| WO | WO 98/23244 | 6/1998 |
| WO | WO 98/34513 | 8/1998 |
| WO | WO 98/34616 | 8/1998 |
| WO | WO 98/43642 | 10/1998 |
| WO | WO 98/55514 | 12/1998 |

OTHER PUBLICATIONS

Hausberger, Angela G. and DeLuca, Patrick P. "Characterization of biodegradable poly(D,L–lactide–co–glycolide) polymers and microspheres," Journal of Pharmaceutical & Biomedical Analysis vol. 13 No. 6 pp. 747–760.

Hyder Salman M., et al. "Uterine Expression of Vascular Endothelial Growth Factor is Increased by Estradiol and Tamoxifen," Cancer Research vol. 56 (Sep. 1, 1996), pp. 3954–3960.

Kimura, Hideya, et al. "A New Vitreal Drug Delivery System Using an Implantable Biodegradable Polymeric Device," Invest Ophthalmol Vis Sci vol. 35 (May 1994) No. 6 pp. 2815–2819.

Langer, Robert. "1994 Whitaker Lecture: Polymers for Drug Delivery and Tissue Engineering," Ann Biomed Eng vol. 23 (Mar.–Apr. 1995) No. 2 pp. 101–111.

Lowe Philip J. and Temple Cathy S. "Calcitonin and Insulin in Isobutylcyanocrylate Nanocapsules: Protection Against Proteases and Effect on Intestinal Absorption in Rats," J Pharm Phamacol vol. 46 (1994) No. 7 & pp. 547–552.

Mangrulkar Rajesh S., et al. "Isolation and Characterization of Heparin–Binding Growth Factors in Human Leiomyomas and Normal Myometrium," Biology of Reproduction vol. 53 (1995) pp. 636–646.

Meikle, M.C., et al. "Bone–derived growth factor release from poly(alpha–hydroxy acid) implants in vitro," Biomaterials vol. 14 (1993) No. 3 pp. 177–183.

Mills GV, et al. "Suramin prevents binding of interleukin 2 to its cells surface receptor: a possible mechanism for immunosuppression," Cancer Res (1990) vol. 50, p. 3036.

Min, Yan–Gi, MD, et al. "Mucociliary Activity and Histopathology of Sinus Mucosa in Experimental Maxillary Sinusitis: A Comparison of Systemic Administration of Antibiotic and Antibiotic Delivery by Polylactic Acid Polymer," Laryngoscope vol. 105 (Aug. 1995) pp. 835–842.

Orloff, Lisa A., et al. "Prevention of venous thrombosis in microvascular surgery by transmural release of heparin from a polyanhydride polymer," Surgery vol. 117 (May 1995) No. 5 pp. 554–559.

Payne, Lendon, et al. "Water–Soluble Phosphazene Polymers for Parenteral and Mucosal Vaccine Delivery," Vaccine Design: The Subunit and Adjuvant Approach, eds. Michael F. Powell and Mark J. Newman, 1995, pp. 473–493.

Sawada, Y., et. al. "An evaluation of a new lactic acid polymer drug delivery system: a preliminary report," British J of Plastic Surgery vol. 47 (1994)pp. 158–161.

Shantha, K.L., et al. "Azo polymeric hydrogels for colon targeted drug delivery," Biomaterials vol. 16 (1995) No. 17 pp. 1313–1318.

Shiino, Daijiro, et al. "Preparation and characterization of a glucose–responsive insulin–releasing polymer device," Biomaterial vol. 15 (1994) No. pp. 121–128.

Shikani, Alan H., et al. "Polymer Delivery of Chemotherapy for Squamous Cell Carcinoma of the Head and Neck," Arch Otolaryngol Head Neck Surg vol. 120 (Nov. 1994) No. 11 pp. 1242–1247.

Singh, Manmohan, et al. "Biodegradable Delivery System for Birth Control Vaccine: Immunogenicity Studies in Rats and Monkeys," Pharm Res vol. 12 (Nov. 1995) No. 11 pp. 1796–1800.

Anania, C.A., et al. "Human Endometrial, Myometrial and Leiomyoma Cells Express an Alternative Spliced Form of Fibroblast Growth Factor Receptor Type I, (abstract)" J Soc Gynecol Invest vol. 2, No. 2, p. 415.

Benezra M, et al. "Antiproliferative activity to vascular smooth muscle cells and receptor binding of heparin–mimicking polyaroatic anionic compounds," Arterioscler Thromb (1994) vol. 14, p. 1992.

Bidan, G., et al. "Incorporation of sulphonated cyclodextrins into polypyrrole: an approach for the electro–controlled delivering of neutral drugs," Biosensors & Bioelectronics vol. 9 (1994) pp. 219–229.

Cascone, Maria Grazia, et al. "Blends of synthetic and natural polymers as drug delivery systems for growth hormone," Biomaterials vol. 16 (1995) No. 7 pp. 569–574.

Cullinan–Bove Kathleen and Koos Robert D. "Vascular Endothelial Growth Factor/Vascular Permeability Factor Expression in the Rat Uterus: Rapid Stimulation by Estrogen Correlates with Estrogen–Induced Increases in Uterine Capillary Permeability and Growth," Endocrinology vol. 133, No. 2, pp. 829–837.

Edelman, Elazer R., et al. "c–myc in Vasculoproliferative Disease," Circ Res vol. 76 (Feb. 1995) No. 2, pp. 176–182.

Fernig DG, et al. "Rat mammary myoepithelial–like cells in culture possess kinetically distinct low–affinity receptors for fibroblast growth factor that modulate growth stimulatory responses," Growth Factors (1992) vol. 7, p. 27.

Giudice Linda C. "Growth factors and growth modulators in human uterine endometrium: their potential relevance to reproductive medicine," J American Fertility Society vol. 61 No. 1, pp. 1–17.

Gordon, John D., et al. "Vascular Endothelial Growth Factor (VEGF) and Cyclic Ovarian Angiogenesis, (abstract)" J Soc Gynecol Invest Vol. 2, No.2, p. 415.

Hanneken, Anne and Baird Andrew. "Soluble Forms of the High–Affinity Fibroblast Growth Factor Receptor in Human Vitreous Fluid," Invest Opthalmol Vis Sci vol. 36, pp. 1192–1196.

Hanneken, A., et al. "Identification of soluble forms of the fibroblast growth factor receptor in blood," Proc Natl Acad Sci USA vol. 91 (Sep. 1994) pp. 9170–9174.

Spencer, Thomas E.., et al. "Ovine Interferon–tau Inhibits Estrogen Receptor U–Regulation and Estrogen–Induced Luteolysis in Cyclic Ewes," Endocrinology vol. 136, No. 11, pp. 4932–4944.

Stein, CA, et al. "Suramin: an anticancer drug with a unique mechanism of action," J Clin Oncol (1998) vol. 7, p. 499.

* cited by examiner

Collagen I (α1)

Collagen III (α1)

| Pirfenidone treatment | LDH (mU/ml/1,000 cells) | |
| --- | --- | --- |
| | Leiomyoma | Myometrium |
| 0mg/ml | 1104±138 | 1126±532 |
| 0.01mg/ml | 913±69 | 588±196 |
| 0.1mg/ml | 988±188 | 519±248 |
| 0.3mg/ml | 1363±83 | 799±420 |
| 1mg/ml | 1040±238 | 1236±426 | each value represents Mean±SD

Figure 11

|   | Pirfenidone treatment | Cell Counts (d. 7) | | % Dead Cells (d. 7) | |
|---|---|---|---|---|---|
|   |   | Leiomyoma | Myometrium | Leiomyoma | Myometrium |
| 1 | 0 mg/ml | 380,000 | 630,000 | 9.0 | 3.0 |
|   | 0.01 mg/ml | 315,000 | 670,000 | 8.0 | 2.5 |
|   | 0.1 mg/ml | 205,000 | 410,000 | 10.0 | 5.0 |
|   | 0.3 mg/ml | 170,000 | 420,000 | 6.0 | 4.0 |
|   | 1.0 mg/ml | 69,000 | 200,000 | 16.0 | 10.0 |
| 2 | 0 mg/ml | 200,000 | 1,130,000 | 7.6 | 3.1 |
|   | 0.01 mg/ml | 228,000 | 1,195,000 | 4.4 | 4.0 |
|   | 0.1 mg/ml | 152,000 | 710,000 | 3.3 | 2.8 |
|   | 0.3 mg/ml | 157,000 | 470,000 | 8.4 | 3.2 |
|   | 1.0 mg/ml | 52,500 | 102,000 | 23.8 | 15.6 |

Figure 12

METHODS AND COMPOUNDS FOR TREATMENT OF ABNORMAL UTERINE BLEEDING

PRIORITY INFORMATION

The present application claims the benefit of priority of U.S. Provisional Patent Applications Serial Nos. 60/027,082 and 60/027,406, both filed Sep. 30, 1996 and of International Application No. PCT/US97/17998, filed Sep. 30, 1997.

SPONSORSHIP

The inventions herein may have resulted, in part, from work performed under National Institutes of Health grant # RO1 HD30496.

BACKGROUND OF THE INVENTION

The invention pertains to medical methods, compounds and devices and, particularly, to the treatment of abnormal uterine bleeding and to improved female contraception.

A common cause of abnormal uterine bleeding is the presence of leiomyomas, or fibroids, in the uterus. The mechanism by which these neoplasms cause abnormal bleeding is not known, but there are several hypotheses. One is that leiomyomas may increase the surface area of the endometrial cavity. Another is that these neoplasms cause changes in the venous structures in the endometrium and myometrium by compressing veins which results in venule ectasia. Abnormal uterine bleeding is also associated with the occurrence of endometrial polyps, adenomyosis, peri-menopausal hormonal transition, as well as idiopathic bleeding (i.e., bleeding for which there is no obvious cause). Furthermore, abnormal uterine bleeding often results from the use of progestin-only contraceptives.

Current therapies for abnormal uterine bleeding are limited. Surgical therapies include hysterectomies, myomectomies, and endometrial ablation. These therapies require anaesthesia and can result in significant morbidity and, rarely, mortality. According to a study by Wilcox et al, based on figures from 1988–1989, approximately forty percent (40%) of the 1.7 million women who have had hysterectomies each year in the United States have a diagnosis related to abnormal uterine bleeding.

Current non-surgical therapies for abnormal uterine bleeding focus on the manipulation of the steroid hormone environment, including, use of oral contraceptives, GnRH agonists and antagonists, and progestins. These therapies result in limited efficacy and/or a significant impact on other steroid hormone-dependent tissues, including breast or bone.

Accordingly, an object of this invention is to provide improved methods for medical therapy and, more particularly, improved methods for treating abnormal uterine bleeding.

More particularly, an object of this invention is to provide improved methods for treating abnormal uterine bleeding that are non-surgical and that do not have detrimental side effects on other bodily tissues, such as, bone, cardiovascular function and breast tissue.

A further object of the invention is to provide such methods as can be effected using known compounds that are already approved for clinical use in humans.

Still another object is to provide such methods as can be applied locally to the uterus and that are reversible.

Yet another object of the invention is to provide improved methods, compounds and devices for female contraception.

A further object of this invention is to provide improved devices and agents for treating abnormal uterine bleeding that are minimally invasive.

A still further object of the invention is to provide such apparatus and agents that can be deployed by the patient, without assistance from a health care professional.

Yet another object is to provide systems for non-surgical treatment of abnormal uterine bleeding that utilize low-cost delivery technologies.

SUMMARY OF THE INVENTION

The foregoing objects are among those met by the invention which provides, in one aspect, medical methods for treating abnormal uterine bleeding via application of compounds that block uterine epithelial, stromal or leiomyoma cell response to angiogenic growth factors by interfering with the growth factors themselves, by blocking receptors in the uterine epithelial or stromal cells to those growth factors, and/or by inhibiting other receptors to those growth factors. For sake of convenience, uterine epithelial, stromal and leiomyoma cells are collectively and individually referred to throughout this document as uterine stromal cells).

The compounds include interferons, particularly type I interferons, pirfenidone, heparin, heparin-like polyaromatic anionic compounds, heparin-sulfate-based compounds, secreted or soluble FGF receptors, and/or RGD-peptide. The angiogenic growth factors to which response is blocked, and their receptors, include basic fibroblast growth factor (bFGF), FGF receptors (FGFR), e.g., FGF receptor 1 (FGFR 1) and FGF receptor 2 (FGFR 2), acidic fibroblast growth factor (aFGF), transforming growth factor β (TGF-β), platelet-derived growth factor (PDGF), heparin binding epi-dermal growth factor (HBEGF), vascular endothelial growth factor (VEGF), parathyroid hormone-related protein (PTHrP) and/or prolactin.

The methods contemplate introducing the aforementioned response-blocking compounds into the body of a patient either systemically, e.g., via injection or implant, or locally to the uterus, e.g., via medicated intrauterine devices, foams and the like.

In related aspects, the invention provides improved formulations for treatment of abnormal uterine bleeding. These comprise the aforementioned response-blocking compounds in solutions, gels, foams or other biologically compatible bases, that release the compounds immediately or via time-release into the patient's body. The formulations can be used for systemic or local treatment.

In still other related aspects, the invention provides devices for treatment of abnormal uterine bleeding. These include interuterine devices (IUD's), intravaginal devices (IVD's), cervical caps, diaphragms, intravaginal creams or foams, and/or intravaginal dissolving capsules containing the aforementioned response-blocking compounds.

Other aspects of the invention provide improved female contraceptive methods that reduce the likelihood of conception while, at the same, avoiding the heretofore common side effect of uterine bleeding. The methods contemplate introducing into a patient a progestin-based, and preferably progestin-only, contraceptive substance, and an angiogenic growth factor receptor blocker (e.g., interferon, pirfenidone, heparin, heparin-like polyaromatic anionic compounds, heparin-sulfate-based compounds, secreted or soluble FGF receptors, and/or RGD-peptide) as described above. These contraceptive substance and response-blocking compounds, which can be administered at differing times or concomitantly with one another, are introduced into the patient systemically or locally.

Further aspects of the invention provide contraceptive formulations, and apparatus for delivering the same, comprising the progestin-based contraceptive substances and responseblocking compounds, as discussed above.

These and other aspects of the invention are evident in the attached drawings and in the description that follows.

BRIEF DESCRIPTION OF THE DRAWINGS

A more complete understanding of the invention may be obtained by reference to the drawings in which:

FIG. 11 shows the effect of pirfenidone treatment on lactate dehydrogenase production by myometrial and leiomyoma cells.

FIG. 12 shows the effect of pirfenidone on cell proliferation and percentage of dead cells.

DETAILED DESCRIPTION OF THE ILLUSTRATED EMBODIMENT

Introduction

A common cause of abnormal bleeding is the presence of leiomyomas, or fibroids, in the uterus. It is asserted that angiogenic growth factors produced and stored in the leiomyomas act on vascular cells and on endometrial cells to cause not only an increase in blood vessel formation in the endometrium, but also to cause a weakening in the endometrial layer.

Figures 1A, 1B:
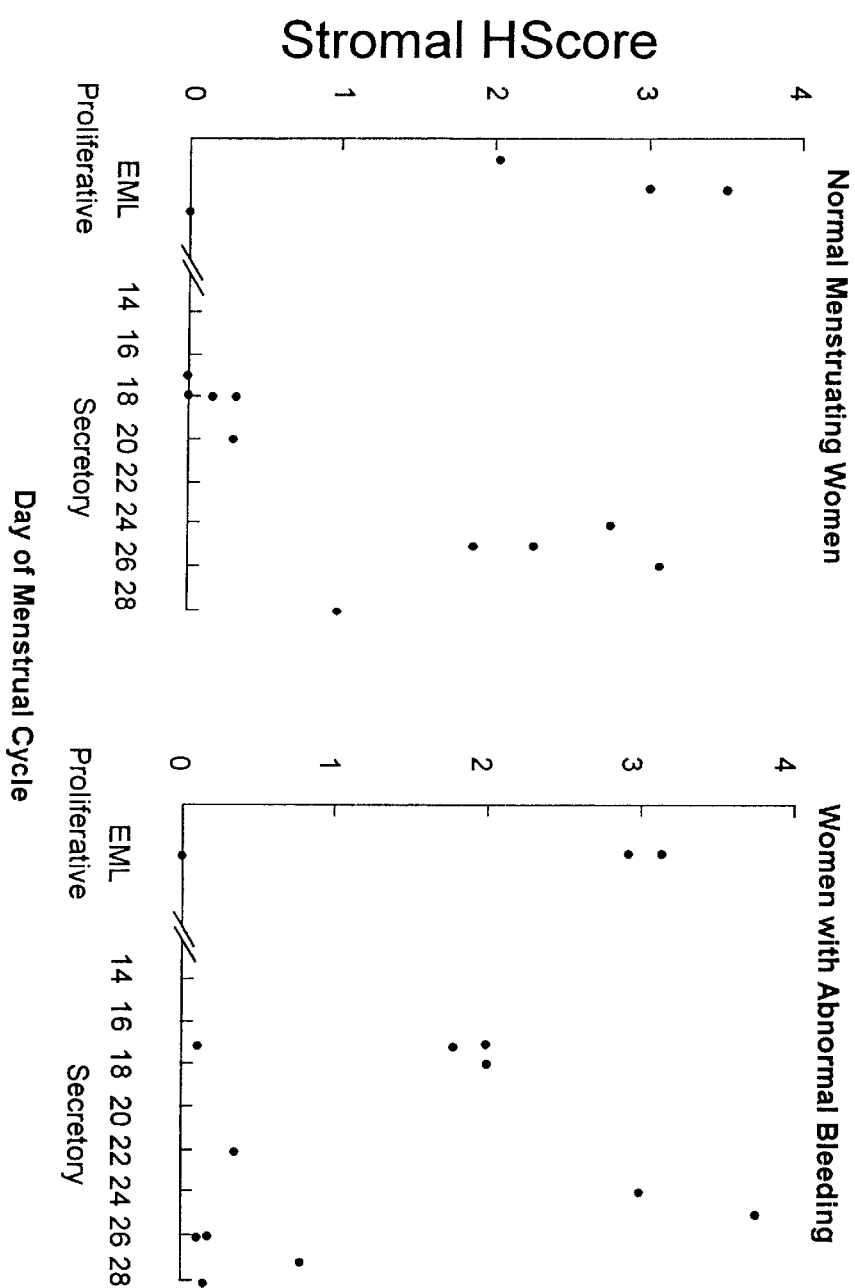
FIG. 1 depicts a HSCORE for immunohistochemical staining of FGFR1 in endometrial stroma.

Myometrium and leiomyomas express the mRNAs and proteins for three heparin-binding angiogenic growth factors: platelet-derived growth factor (PDGF), heparin-binding epidermal growth factor (HBEGF), and basic fibroblast growth factor (bFGF). Leiomyomas show elevated levels of mRNA expression for bFGF when compared to normal myometrium and the immunohistochemistry analysis showed that leiomyomas contain large amounts of bFGF stored in the extracellular matrix (much more than the normal myometrium). Thus, leiomyomas are a source of this potent angiogenic factor that could have significant effects on the endometrium and also contribute to the enhanced growth of these neoplasms. FIG. 1 shows the HSCORE for immunohistochemical staining for FGFR1 in endometrial stroma in women with normal menstrual cycles (A) and leiomyoma-related bleeding (B). A suppression of FGFR1 expression is seen in the normal women that may begin as early as the late proliferative phase and extends through the mid-luteal phase. Significantly, this suppression is absent in most women with abnormal uterine bleeding.

Figures 2A, 2B, 2C, 2D, 2E, 2F, 2G, 2H, 2I, 2J:
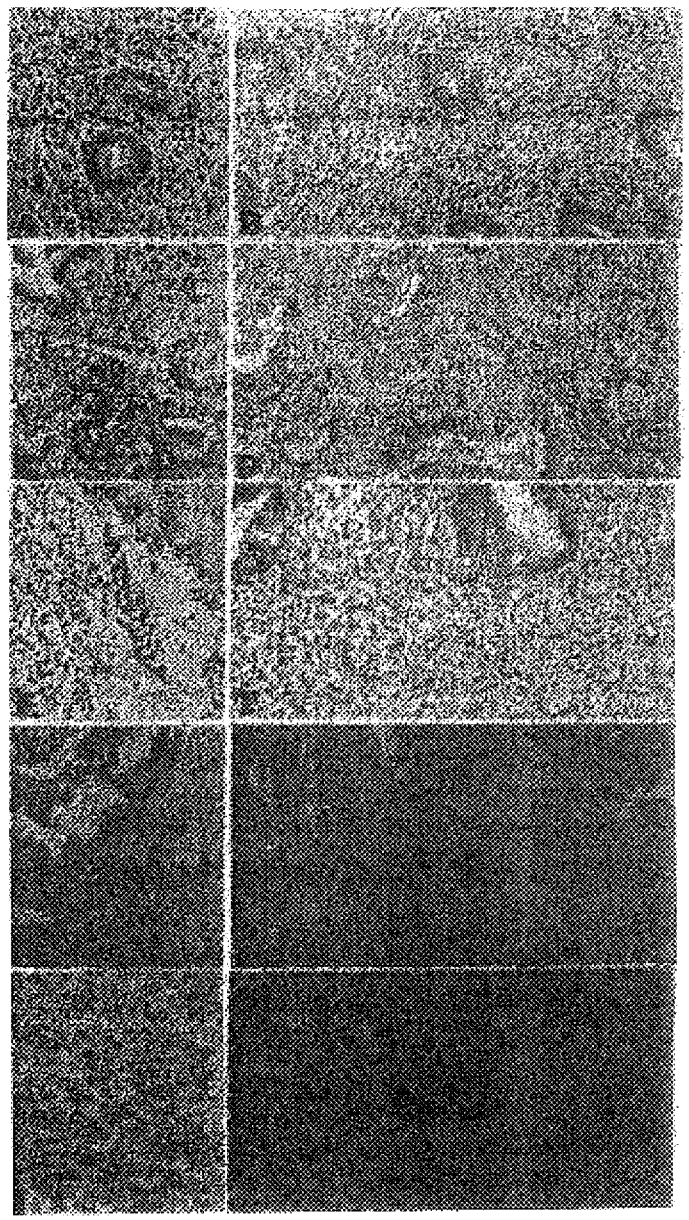
FIG. 2 depicts immunohistochemical localization of FGFR1 in human uterine tissues throughout the menstrual cycle.

Referring to FIG. 2, the expression of the type 1 FGF receptor in uterine endometrium, myometrium and leiomyomas at various stages of the menstrual cycle were analyzed. Tissues were processed for immunohistochemistry and also to RNA for analysis by reverse transcriptase-polymerase chain reaction (RT-PCR). Primers were used to distinguish between the complete form of FGF receptor 1, the alternatively spliced variant lacking the most external immunoglobulin-like domain, and the truncated, secreted form of the receptor. Amplification of cDNAs from all three tissue types revealed the presence of four forms of FGF receptor type 1 including a second secreted form. As shown in FIG. 2, immunohistochemistry for the receptor showed that both leiomyoma and myometrial smooth muscle cells expressed this receptor throughout the menstrual cycle. Results for endometrium showed that the glandular epithelial cells expressed the FGF receptor during the proliferative and early-mid secretory phase of the cycle with somewhat reduced staining at the time of menstruation. In contrast, stromal cells showed strong perinuclear staining during the early proliferative phase of the cycle and again during the late secretory phase when they were undergoing a second wave of proliferation prior to deacidualization.

Based on the foregoing, we have discovered that the various endometrial cell types express the bFGF receptor and that expression varies throughout the menstrual cycle, particularly for the stromal cells. The pattern of expression correlates not only with the two waves of proliferation seen for stromal cells during the cycle, but also with integrin expression.

Figure 3A:
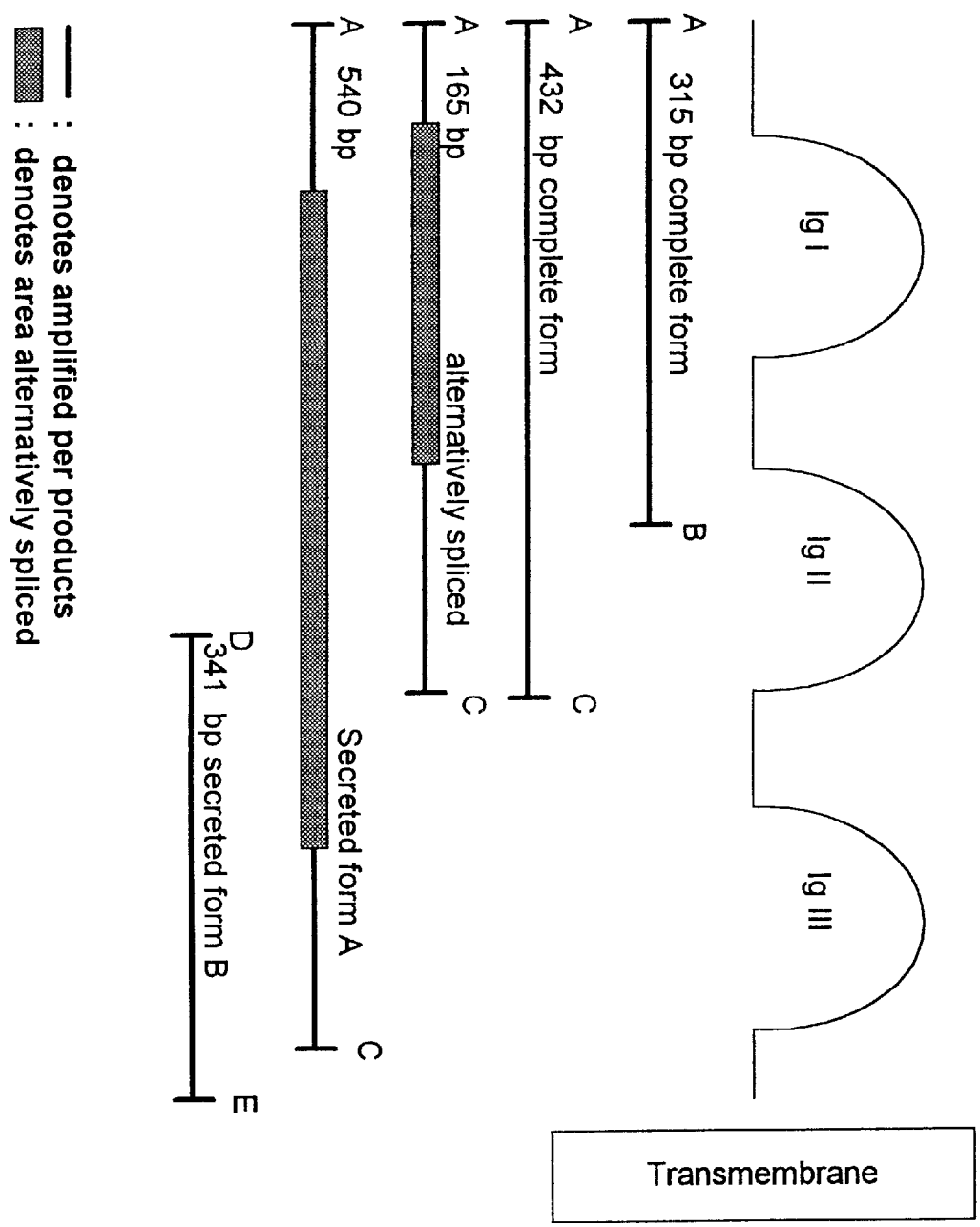
FIG. 3 shows RT-PCR detection of FGFR1 isotypes and a schematic diagram of the primers used and the fragments amplified.
Figures 3B, 3C, 3D:
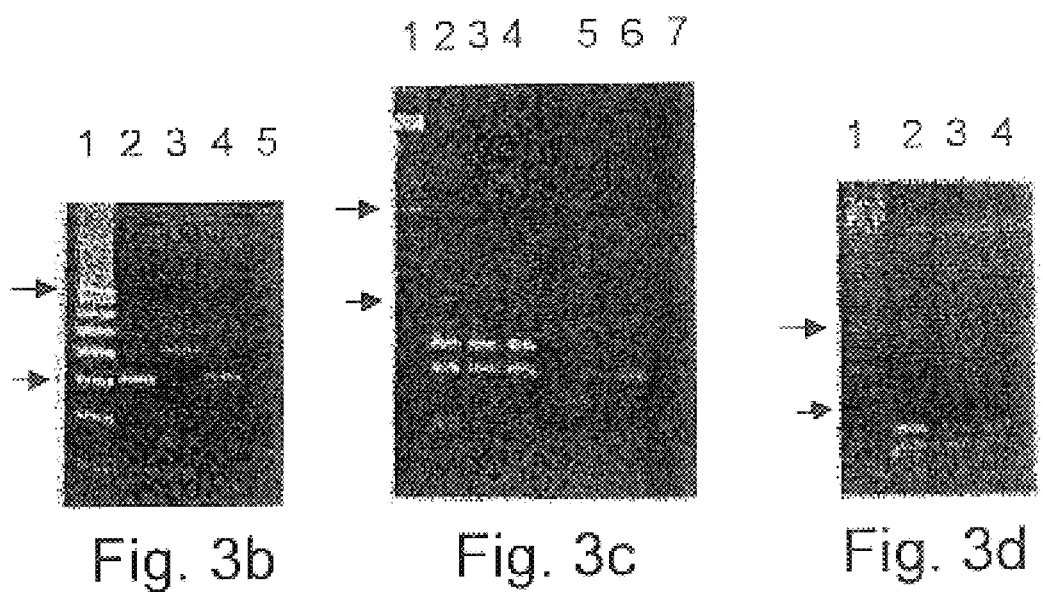
Figure 4:
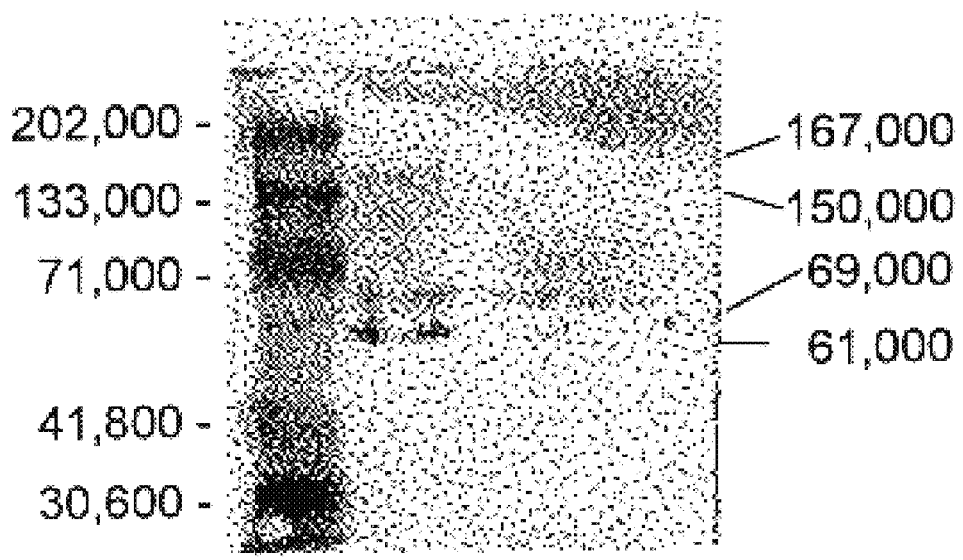
FIG. 4 is a protein immunoblot identifying the two forms of the FGFR1 receptor.

FIG. 3 shows the RT-PCR detection of FGFR1 isotypes and a schematic diagram of the primers used and the fragments amplified. Additionally, FIG. 4 shows the protein immunoblot identifying the two secreted forms of the receptor. The two proteins of 69,000 and 61,000 MW represent the two different secreted forms of the type 1 FGF receptor.

Figure 5A:
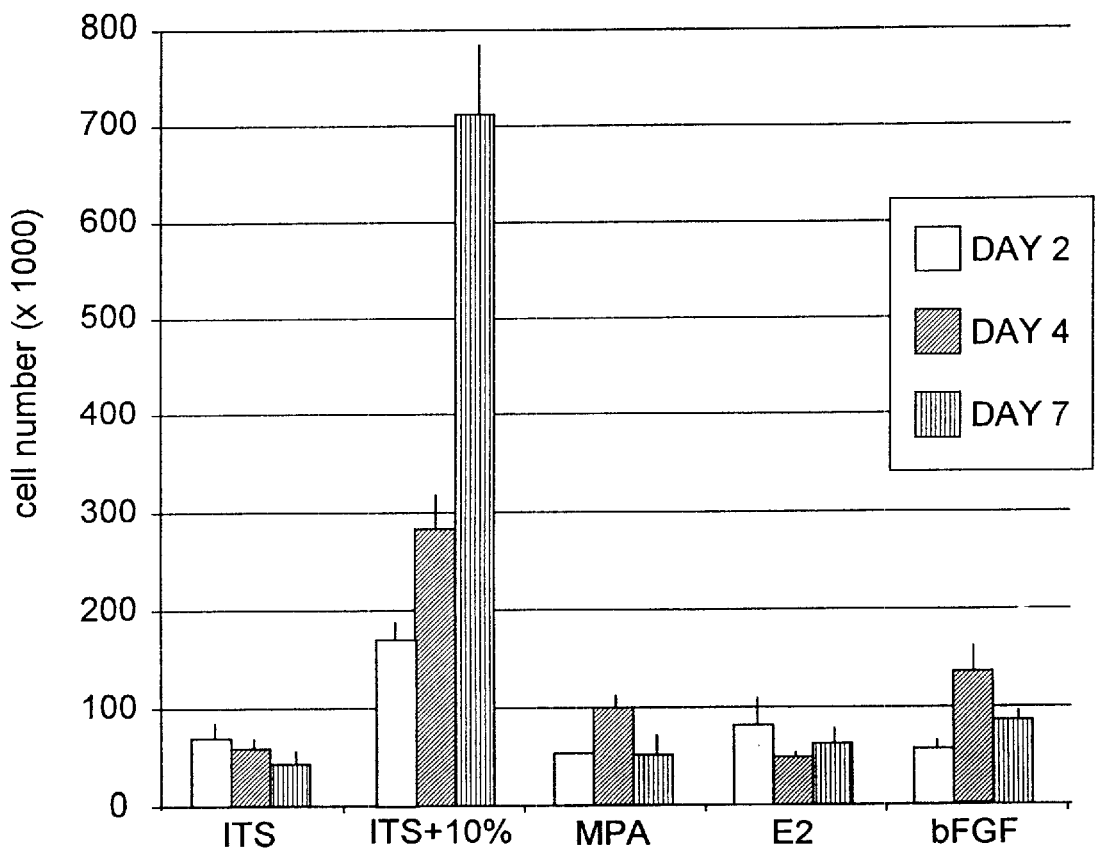
FIGS. 5a and 5b show the effect of bFGF and progesterone on cell proliferation. Increases in cell numbers occured only in the presence of serum or the combination of bFGF and progesterone.
Figure 5B:
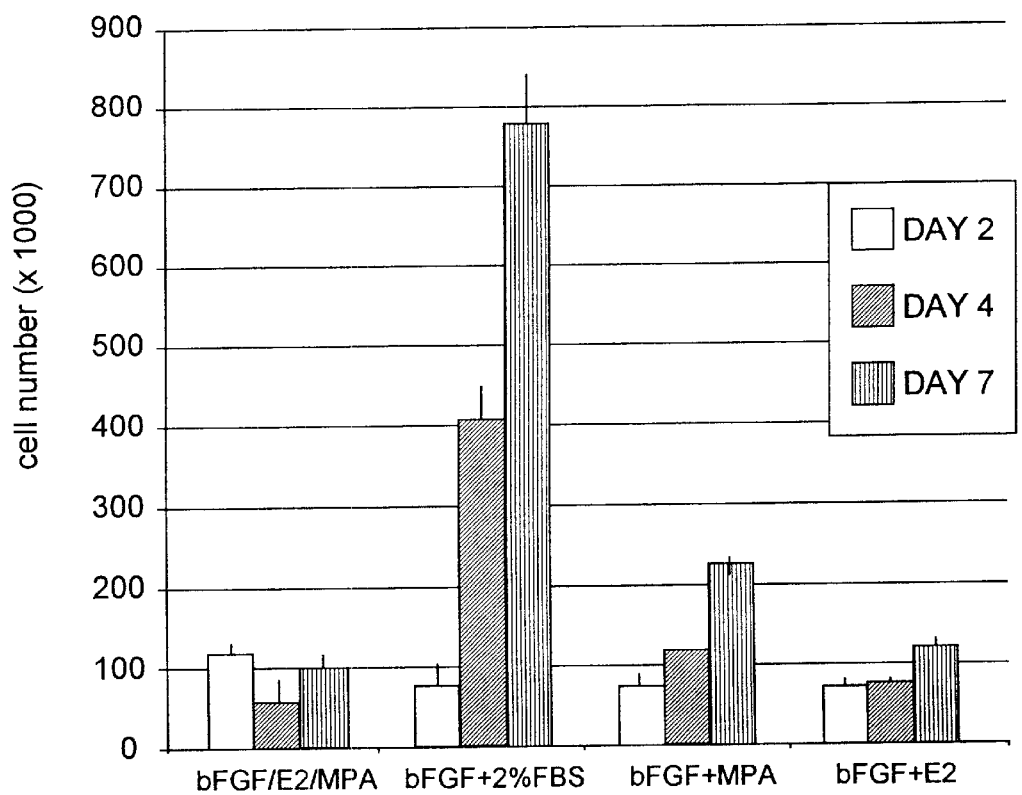

We have also discovered that bFGF stimulates the proliferation of uterine stromal cells in culture but only in the presence of progesterone. FIGS. 5a and 5b show the effect of the cell treatment on the cell number, and reveal that cell proliferation increases only in the presence of serum of with the treatment of bFGF and progesterone.

Therapies, Compounds and Devices for Prevention of Abnormal Uterine Bleeding

As discussed previously, the most common cause of abnormal uterine bleeding is the presence of leiomyomas (fibroids) in the uterus. The mechanism by which these tumors cause abnormal bleeding is not known but there are several hypotheses. One is that leiomyomas may increase the surface area of the endometrial cavity. Another theory is that these tumors cause changes in the venous structures in the endometrium and myometrium by compressing veins which results in venule ectasia. Studies have shown that leiomyomas have an enriched arterial supply and that the surrounding myometrial tissue has a great increase in the venus plexus.

These observations suggest that there is an increase in angiogenesis in the uterus containing leiomyomas. We assert that angiogenic growth factors produced and stored in the leiomyomas act on vascular cells and on endometrial cells to cause not only an increase in blood vessel formation in the endometrium, but also to cause a weakening in the endometrial layer through changes in matrix production and turnover, and that this leads to increased bleeding.

Other causes of abnormal uterine bleeding include adenomyosis, progestin only contraceptives, endometrial polyps, and there is also perimenopausal abnormal uterine bleeding. Some women have idiopathic abnormal uterine bleeding which means there is no obvious case. We assert that alterations in the normal pattern of angiogenic growth factor production or expression of the receptors for these growth factors by uterine cells are the underlying cause for all these abnormal uterine bleeding pathologies.

Insofar that certain angiogenic growth factors such as bFGF are involved in the pathology of abnormal uterine bleeding, we have additionally discovered that compounds which inhibit the synthesis of bFGF or inhibit its actions may be used for treatment of this problem.

Accordingly, one embodiment of the invention provides a method of treating abnormal uterine bleeding by introducing into the patient compounds that block expression of the following growth factors (or ligands), by blocking their binding to receptors in the uterine stromal cells, and/or by inhibiting other receptors to the ligands (such as the low affinity receptor heparin sulfate that plays a role in binding bFGF to the stromal cells): (i) basic fibroblast growth factor (bFGF), (ii) fibroblast growth factor receptor 1 (FGFR1), (iii) angiogenic growth factors, such as acidic fibroblast growth factor (aFGF), transforming growth factor β (TGF-β), platelet-derived growth factor (PDGF), heparin binding epidermal growth factor (HBEGF), vascular endothelial growth factor (VEGF), parthyroid-related protein (PTHrP) and/or prolactin. These compounds include interferons, particularly type I interferons, pirfenidone, heparin, heparin-like polyaromatic anionic compounds, heparin-sulfate-based compounds, secreted or soluble FGF receptors, and/or RGD-peptide.

In practice of this embodiment of the invention, one or more of these compounds is administered systemically or locally to the patient. Systemic administration can be accomplished, e.g., via ingestion of a pill or capsule, though it is preferably accomplished via intravenous, intramuscular or subcutaneous injection or subcutaneous implantation, to avoid undue breakdown of the compound(s) in the digestive tract. Intramuscular or subcutaneous injections are preferably administered in the abdominal region. Still more preferably, one or more of the foregoing response-blocking compounds are applied locally to the uterus, for example, via a medicated intrauterine device (IUD), intravaginal device (IVD), cervical cap, diaphragm, intravaginal cream or foam and/or intravaginal dissolving capsules of the type shown in FIGS. 15A–15C.

Regardless of whether they are administered systemically or locally, one or more of the aforementioned compounds are administered so that dosages in the range of 1 to 10,000 U/ml and, preferably, 100 to 1000 U/ml of the compounds are present in the bodily tissues and/or fluids surrounding the uterine stromal cells.

Thus, according to one practice of the invention, 0.25 mg dosages of Betaseron (interferon) are administered subcutaneously every other day, e.g., for a period of 1 to 30 days and, preferably, 3 to 10 days, in order to inhibit or reduce abnormal uterine bleeding. Other interferons, pirfenidone, heparin, heparin-like polyaromatic anionic compounds, heparin-sulfate-based compounds, secreted or soluble FGF receptors, and/or RGD-peptide can be administered in lieu of, or in addition to Betaseron, in functionally equivalent dosages to inhibit or reduce abnormal such bleeding. Those skilled in the art will appreciate that these and other dosages of the aforementioned compounds may also be administered subject to the constraint that potentially toxic dosages are avoided. In instances where multiple compounds are utilized, e.g., interferon and heparin, those compounds can be administered concomitantly or at different times, e.g., in alternating administrations.

Those skilled in the art will appreciate that, whereas higher dosages are generally appropriate when the aforementioned compounds are administered systemically, lower dosages are generally utilized for local applications, e.g., via medicated IUD's, IVD's, cervical caps, diaphragms, intravaginal creams or foams and/or intravaginal dissolving capsules. With regard to these vehicles for local application, the compounds can be incorporated for immediate or time-delayed release.

Figure 15A:
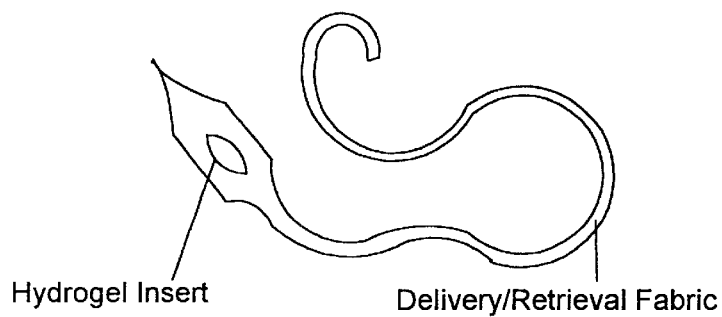
FIGS. 15A–C depict devices and agents for local delivery to the uterus of compounds that block response to angiogenic growth factors and for local delivery of improved contraceptives according to the invention.
Figure 15B:
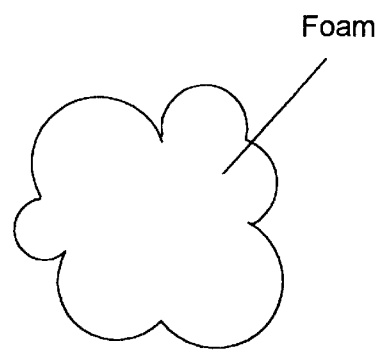
Figure 15C:
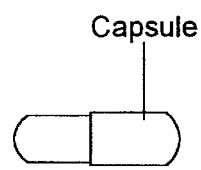

Related embodiments of the invention provide improved formulations and devices of the types illustrated in FIGS. 15A–15C for treatment of abnormal uterine bleeding. These comprise response-blocking compounds of the types described above combined with, or otherwise embodied in, biocompatible bases, inert or otherwise (such as saline solutions or gels, or other formulation known in the art) that permit introduction of the compounds into a patient's body. Those bases may be formulated, and the components incorporated therein, so as to provide for immediate or time-delayed release in the conventional manner known in the art.

As above, dosages are dependent upon the particular response-blocking substances chosen and its intended mechanism for the administration to the patient. Thus, for example, a vaginal foam of the type illustrated in FIG. 15B for local administration may comprise Betaseron, microencapsulated for time-delayed release. Dosages of the interferon are adjusted so that 1 to 10,000 U/ml and, preferably, 100 to 1000 U/ml of the interferon, are present in the tissues and fluids surrounding the uterine stromal cells for periods of 1 to 30 days and, preferably, for periods of 3 to 10 days. As above, other response-blocking compounds, such as other interferons, pirfenidone, heparin, heparin-like polyaromatic anionic compounds, heparin-sulfate-based compounds, secreted or soluble FGF receptors, and/or RGD-peptide administered in lieu of, or in addition to Betaseron.

FIG. 15A depicts a vaginal insert according to the invention for delivery of one or more of the aforementioned response-blocking compounds. The insert, which has a structure similar to the Cervidil product of Forest Pharmaceuticals, comprises a hydrogel insert contained within a knitted retrieval system formed in the manner of a shoelace. The hydrogel insert contains the response-blocking compound, which is microencapsulated in the conventional manner for time-delayed release at the dosages and for the periods discussed above.

A device of the type illustrated in FIG. 15A is placed transversely at the posterior fornix of the vagina. In this environment, the hydrogel insert releases the compound for a desired treatment period. Multiple hydrogel inserts with varying release rates can be utilized to provide long-term treatment.

FIG. 15C depicts an intravaginal dissolving capsule according to the invention for delivery of one or more of the aforementioned response-blocking compounds. The capsule, comprising a gelatin shell, holds one or more such compounds microencapsulated for time-delayed release at the dosages and for the periods discussed above.

Those skilled in the art will appreciate that the mechanisms illustrated in FIGS. 15A–15C for delivery of response-blocking compounds in treatment of abnormal uterine bleeding according to the invention are illustrative only and that those compounds can be embodied in other bases and/or vehicles commonly known for delivery of substances to the human body.

Improved Therapies, Compounds and Devices for Female Contraception

Recognizing that the response-blocking compounds enumerated above can prevent abnormal uterine bleeding, we have devised improved female contraceptive therapies, compounds and devices that inhibit abnormal uterine bleeding otherwise associated with progestin and progestin-based contraceptives.

According to one practice of the invention, a method of female contraception includes administering to the patient progestin (or a progestin-based contraceptive substance) along with one or more of the following response-blocking compounds: interferon, particularly type I interferons, pirfenidone, heparin, heparin-like polyaromatic anionic compounds, heparin-sulfate-based compounds, secreted or soluble FGF receptors, and/or RGD-peptide. As currently understood by the inventors, these response-blocking compounds prevent or reduce abnormal uterine bleeding otherwise caused by progestin and, particularly, by the undue expression of the certain growth factors or undue affinity thereto in the uterine stromal cells effected by those substances. These growth factors include (i) basic fibroblast growth factor (bFGF), (ii) fibroblast growth factor receptor 1, (iii) angiogenic growth factors, such as acidic fibroblast growth factor (aFGF), transforming growth factor β (TGF-β), platelet-derived growth factor (PDGF), heparin binding epidermal growth factor (HBEGF), vascular endothelial growth factor (VEGF), parthyroid-related protein (PTHrP) and/or prolactin.

In practice of an improved method for female contraception according to the invention, a medication containing one or more of the foregoing response-blocking compounds is administered systemically or locally to the patient in connection with the administration of progestin or a progestin-based contraceptive substance, e.g., the progestin-only contraceptives Depo-Provera, Norplant, Levonorgestrel-containing IUD, Progestesert. The progestin-based substance is introduced to the patient in the conventional manner known thereto, such as by ingestion, injection, subcutaneous implant or cavity implant (e.g., medicated IUD, IVD, suppository, cervical cap, diaphragm, intravaginal cream or foam, intravaginal dissolving capsules, or the like). The aforementioned response-blocking compounds are administered systemically or locally in the manners and dosages described above. Such administration can be concomitant with, or at varying times from, the contraceptive substance.

Thus, in one practice of the invention, a progestin-only contraceptive (e.g., Depo-Provera) is administered to a patient in the conventional manner, while the patient is concurrently dosed with a response-blocking compound in the manner described above (e.g., 0.25 mg dosages of Betaseron administered every two days, or other interferons, pirfenidone, heparin, heparin-like polyaromatic anionic compounds, heparin-sulfate-based compounds, secreted or soluble FGF receptors, and/or RGD-peptide administered in lieu of, or in addition to Betaseron) to avoid conception and to inhibit the bleeding otherwise caused by the progestin-only contraceptive. Those skilled in the art will appreciate that other dosages of the response-blocking compounds may be required, depending on the specific progestin-based substance used, its dosage and the patient's reaction thereto.

A further embodiment of the invention provides an improved contraceptive compound comprising progestin or a progestin-based (and, preferably, a progestin-only) contraceptive substance, in combination with a response-blocking compound of the type described above. These components are combined with one another and, optionally, embodied in a biocompatible base, inert or otherwise, such as saline solutions or gels, or other formulation known in the art, to provide an improved female contraceptive compound that does not cause abnormal uterine bleeding. Those bases may be formulated, and the components incorporated therein, so as to provide for immediate or time-delayed release in the conventional manner known in the art.

Relative and actual dosages are dependent upon the particular contraceptive substances and response-blocking substances used and on the intended mechanism for the administration to the patient. Thus, for example, a contraceptive foam of the type illustrated in FIG. 15B for local administration of a female contraceptive according to the invention may comprise progestin and Betaseron, both microencapsulated for time-delayed release. Dosages of the progestin are adjusted in accord with the conventional manner known in the art. Dosages of the interferon are adjusted so that 1 to 10,000 U/ml and, preferably, 100 to 1000 U/ml of the interferon, are present in the blood or other bodily tissue and/or fluids surrounding the uterine stromal cells for at least the period during which the progestin is active in the patient's body. As above, other response-blocking compounds, such as other interferons, pirfenidone, heparin, heparin-like polyaromatic anionic compounds, heparin-sulfate-based compounds, secreted or soluble FGF receptors, and/or RGD-peptide administered in lieu of, or in addition to Betaseron).

FIG. 15A depicts a vaginal insert according to the invention for improved contraception. The insert, which too has a structure similar to the Cervidil product of Forest Pharmaceuticals, comprises a hydrogel insert contained within a knitted retrieval system formed in the manner of a shoelace. The hydrogel insert contains a contraceptive formulation of the type described above, containing progestin (or other progestin-based contraceptive substance) and a response-blocking response-blocking compound as herein described. As above, the formulation is microencapsulated in the conventional manner for time-delayed release at the dosages and for the periods discussed above. The device of FIG. 15 is utilized in the manner described above for administration of the formulation.

FIG. 15C likewise depicts an intravaginal dissolving capsule according to the invention for delivery of such a contraceptive formulation. The capsule, comprising a gelatin shell, contains progestin (or a progestin-based contraceptive substance) and a response-blocking compound of the type described above, microencapsulated for time-delayed release at the dosages and for the periods discussed above.

Those skilled in the art will appreciate that the mechanisms illustrated in FIGS. 15A–15C for delivery of improved female contraceptive formulations according to the invention are illustrative only and that those compounds can be embodied in other bases and/or vehicles commonly known for delivery of substances to the human body.

Procedures for Diagnosing Abnormal Uterine Bleeding

In further embodiments, the invention provides methods for testing and determining the propensity of a female patient to abnormal uterine bleeding. The method comprises applying a labeled angiogenic growth factor receptor blockers, i.e. a labeled response-blocking compound, of the type described above to a biological sample obtained from the patient. Where those blockers (or compounds) shown excessive affinity to the sample, such a propensity is indicated.

More particularly, the method comprises preparing a diagnostic formulation by combining a labeling substance, such as a fluorescent dye, stain, radionucleotide, or the like, with a response-blocking compound, such as an interferon, particularly type I interferons, pirfenidone, heparin, heparin-like polyaromatic anionic compounds, heparin-sulfate-based compounds, secreted or soluble FGF receptors, RGD-peptide, or other such compounds that block expression of the following growth factors, by blocking their binding to receptors in the uterine stromal cells, and/or by inhibiting other receptors to the ligand (such as the low affinity receptor heparin sulfate that plays a role in binding bFGF to the stromal cells): (i) basic fibroblast growth factor (bFGF), (ii) fibroblast growth factor receptor 1, (iii) angiogenic growth factors, such as acidic fibroblast growth factor (aFGF), transforming growth factor $\beta$ (TGF-$\beta$), platelet-derived growth factor (PDGF), heparin binding epidermal growth factor (HBEGF), vascular endothelial growth factor (VEGF), parthyroid-related protein (PTHrP) and/or prolactin. The response-blocking compound is labeled with the labeling substance in the conventional manner known in the art.

The diagnostic formulation is then applied to a biologic sample containing uterine stromal cells obtained from the patient. Preferably, this is done in vitro, e.g., by obtaining a tissue sample from the patient's uterus or other surrogate, such as mucus, blood or vaginal secretions, applying the formulation thereto, and washing to remove excess therefrom. Alternatively, the formulation can be applied in vivo, e.g., where a non-irritating fluorescent or stain is used as the labeling substance, by applying it locally to the uterus and flushing any excess.

Following application of the labeling formulation and removal of excess, the amount of residual is measured, i.e., by quantitatively or qualitatively compared with a norm. Samples that show excessive affinity for the formulation (e.g., as evidenced by darker staining, brighter fluorescence or higher radiological activity) as compared with norms generated from non-afflicted women may be indicative of the patient's propensity to abnormal uterine bleeding. Likewise, samples that show similar affinity for the formulation as compared with norms generated from similarly afflicted women may also be indicative of the patient's propensity to abnormal uterine bleeding. This information can be used in determining an appropriate course of treatment, e.g., application of response-blocking compounds of the types described above.

The so-called norm s used in the foregoing method are prepared by applying the labeling formulation to samples obtained from women with previously diagnosed abnormal uterine bleeding and/or with non-afflicted women. Quantitative or qualitative measurements of labeling activity, following washing or flushing, are recorded for use in comparison with individual patients.

EXAMPLE

We have carried out a number of experiments testing the effects of interferon-$\alpha$ on DNA synthesis in cultured myometrial and leiomyoma cells. The results from a representative experiment are shown in FIGS. 6a and 6b.

Figure 6A:
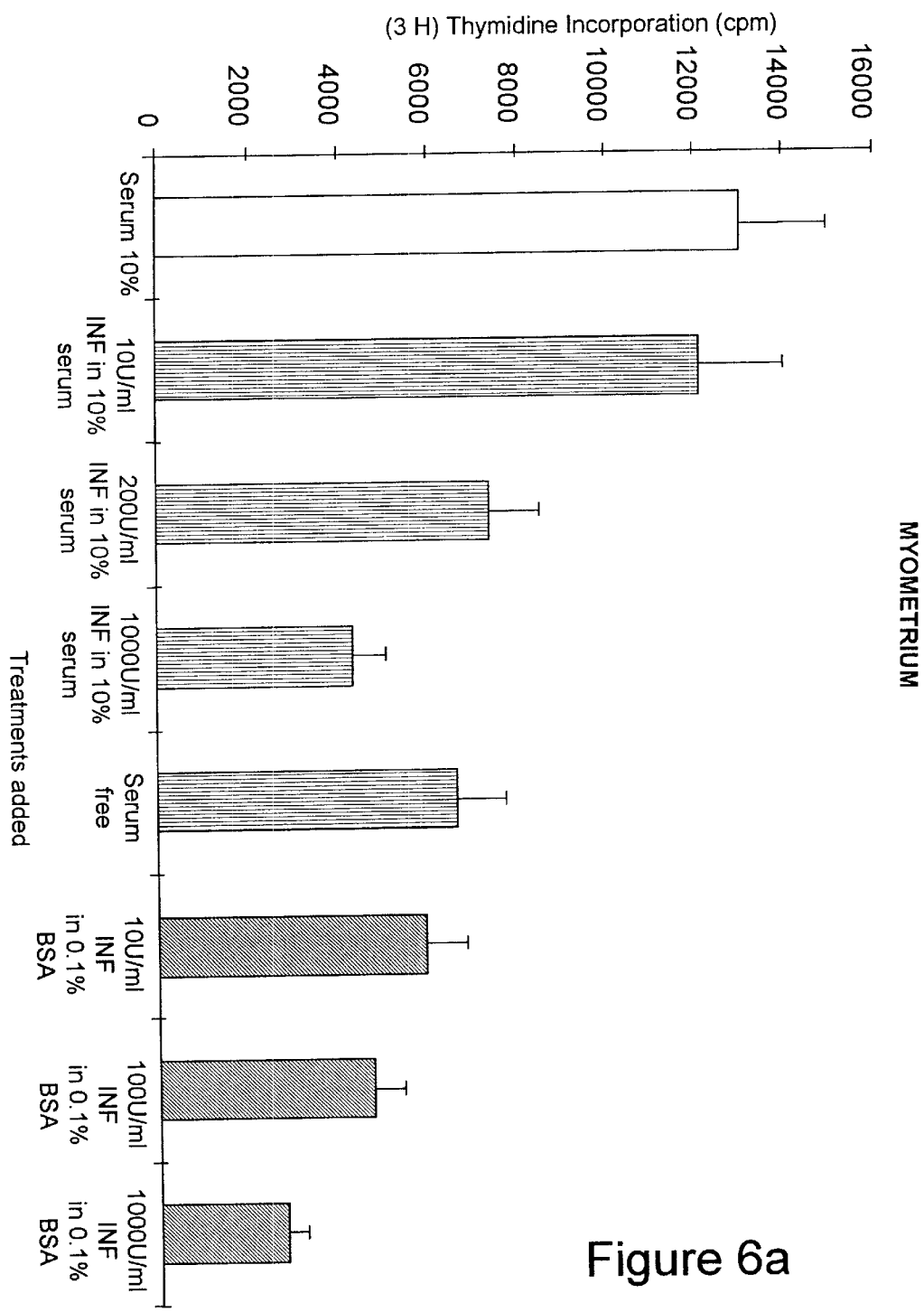
FIGS. 6a–6d show the effects of interferon α on DNA synthesis in cultured myometrial and leiomyoma cells.
Figure 6B:
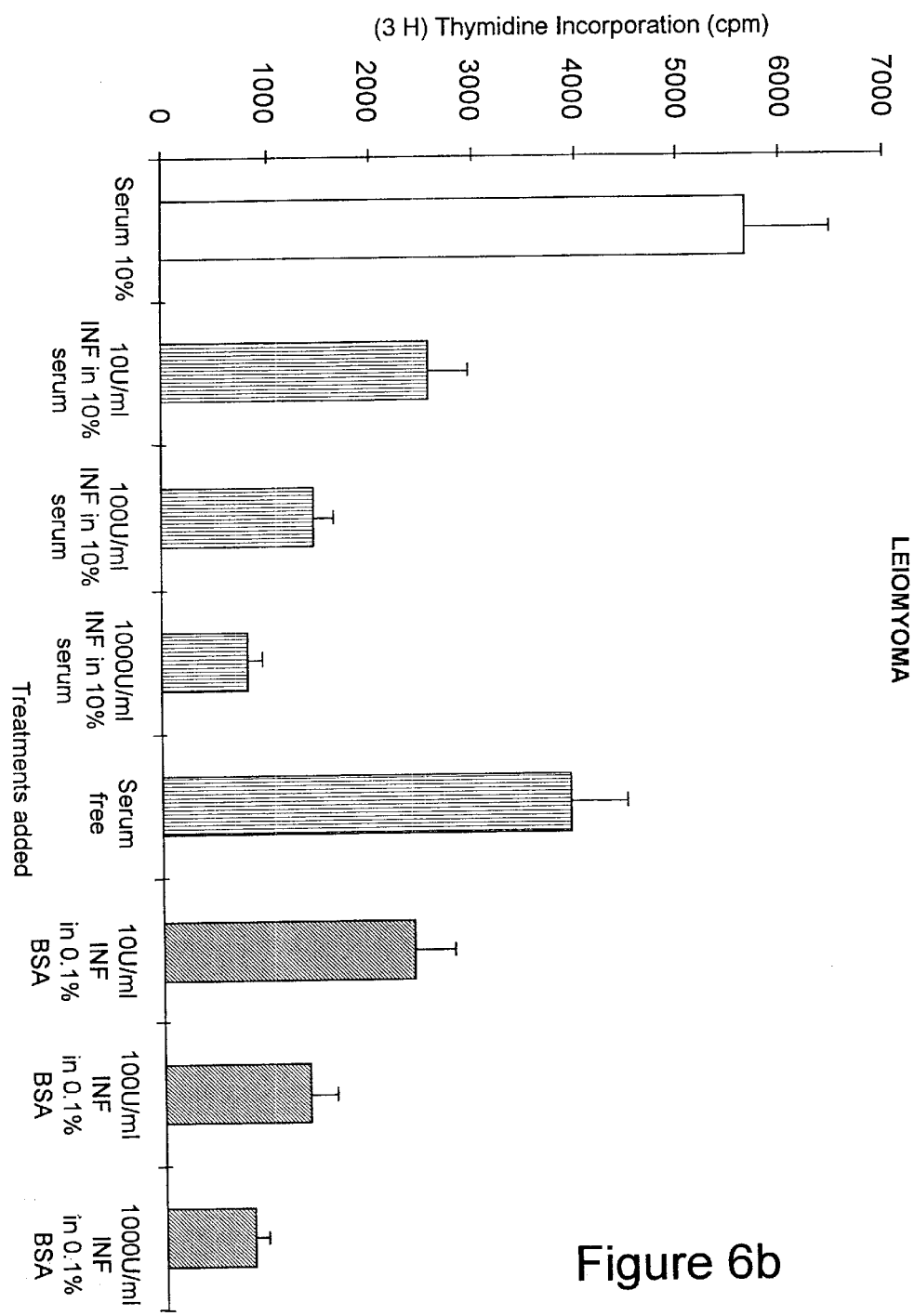

FIG. 6a shows the effect of interferon-$\alpha$ on basal and serum-stimulated DNA synthesis in cultured human myometrial smooth muscle cells. As the concentration of interferon alpha increases, the tritiated thymidine incorporation decreases, thus indicating less basal and serum stimulated DNA synthesis. FIG. 6b shows the effect of interferon-alpha on basal and serum-stimulated DNA synthesis in cultured human leiomyoma smooth muscle cells. Similarly, FIG. 6b also shows that as the concentration of interferon alpha increases, the tritiated thymidine incorporation decreases, indicating less basal and serum stimulated DNA synthesis.

Thus, interferon-$\alpha$ treatment caused a dose-dependent inhibition of DNA synthesis for both normal myometrial and leiomyoma smooth muscle cells. Similar results have been obtained for four separate experiments, and it has been found that both cell types are sensitive to the antiproliferative effects of interferon-$\alpha$.

Figure 6C:
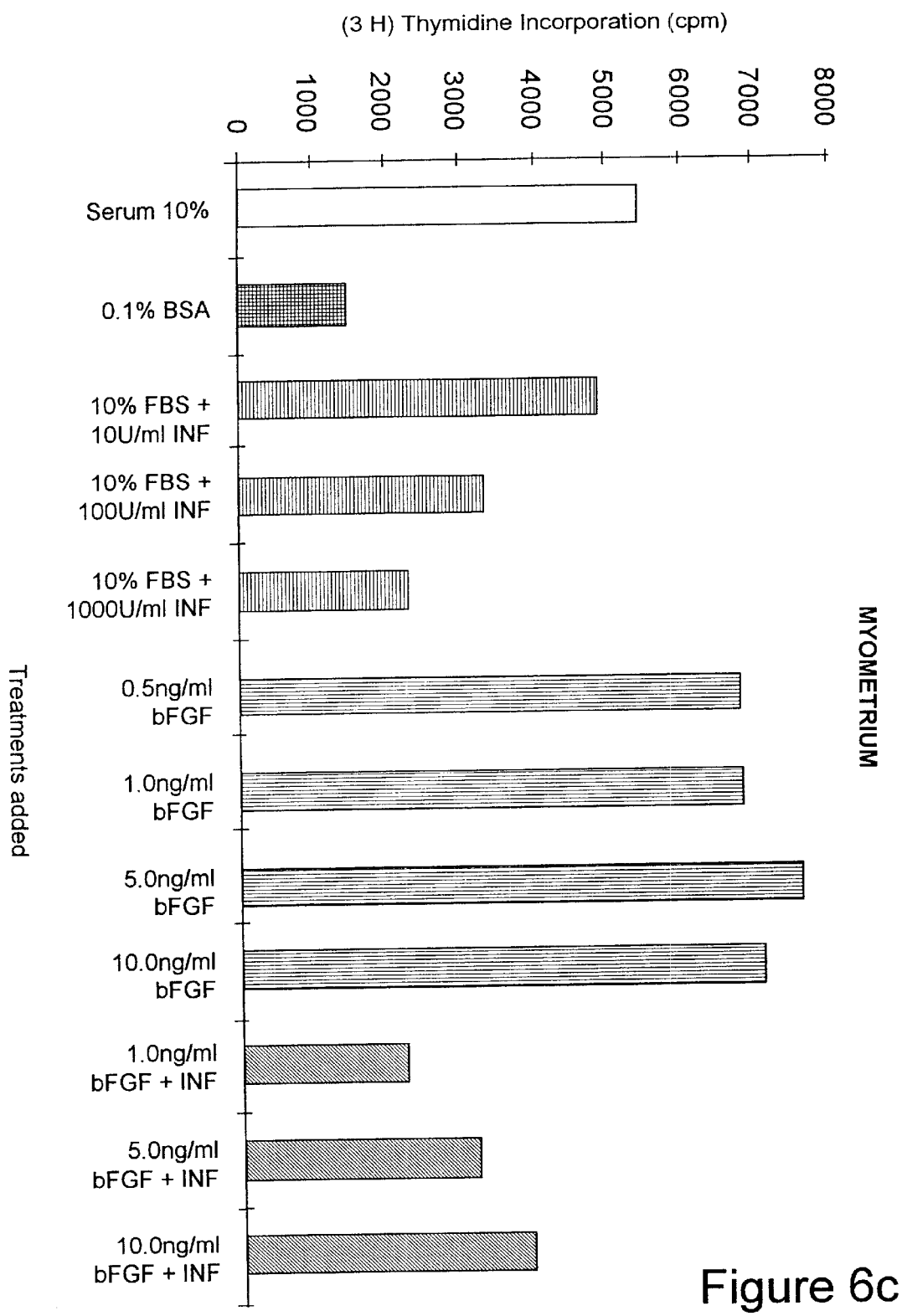
Figure 6D:
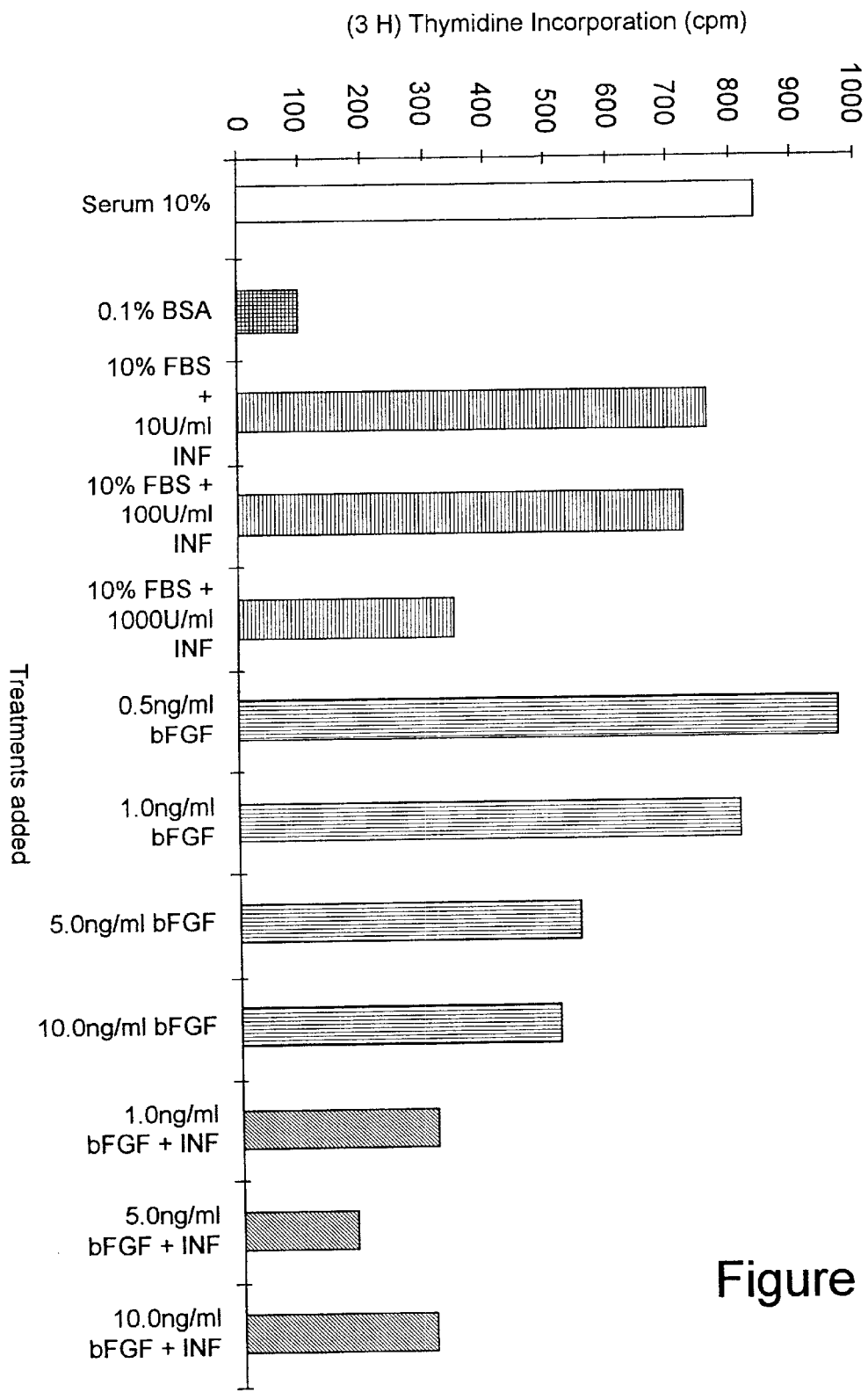

The effects of interferon-$\alpha$ on bFGF induced increases in DNA synthesis by uterine myometrial and leiomyoma cells have also been tested. The results of such an experiment are shown in FIGS. 6c and 6d. Basic FGF caused an increase in DNA synthesis for myometrial smooth muscle cells but had a similar effect on the fibroid (leiomyoma) cells. Concomitant treatment of the myometrial cells with bFGF and interferon-$\alpha$ abolished the stimulating effect on bFGF on DNA synthesis. It appears that interferon $\alpha$ can block bFGF effects on proliferation. FIG. 6c shows the inhibitory effect of interferon-alpha on basic fibroblast growth factor (bFGF) induced DNA synthesis in cultured human myometrial smooth muscle cells. FIG. 6d shows the inhibitory effect of interferon alpha on basic fibroblast growth factor (bFGF) induced DNA synthesis in cultured human leiomyoma smooth muscle cells.

Figure 6E:
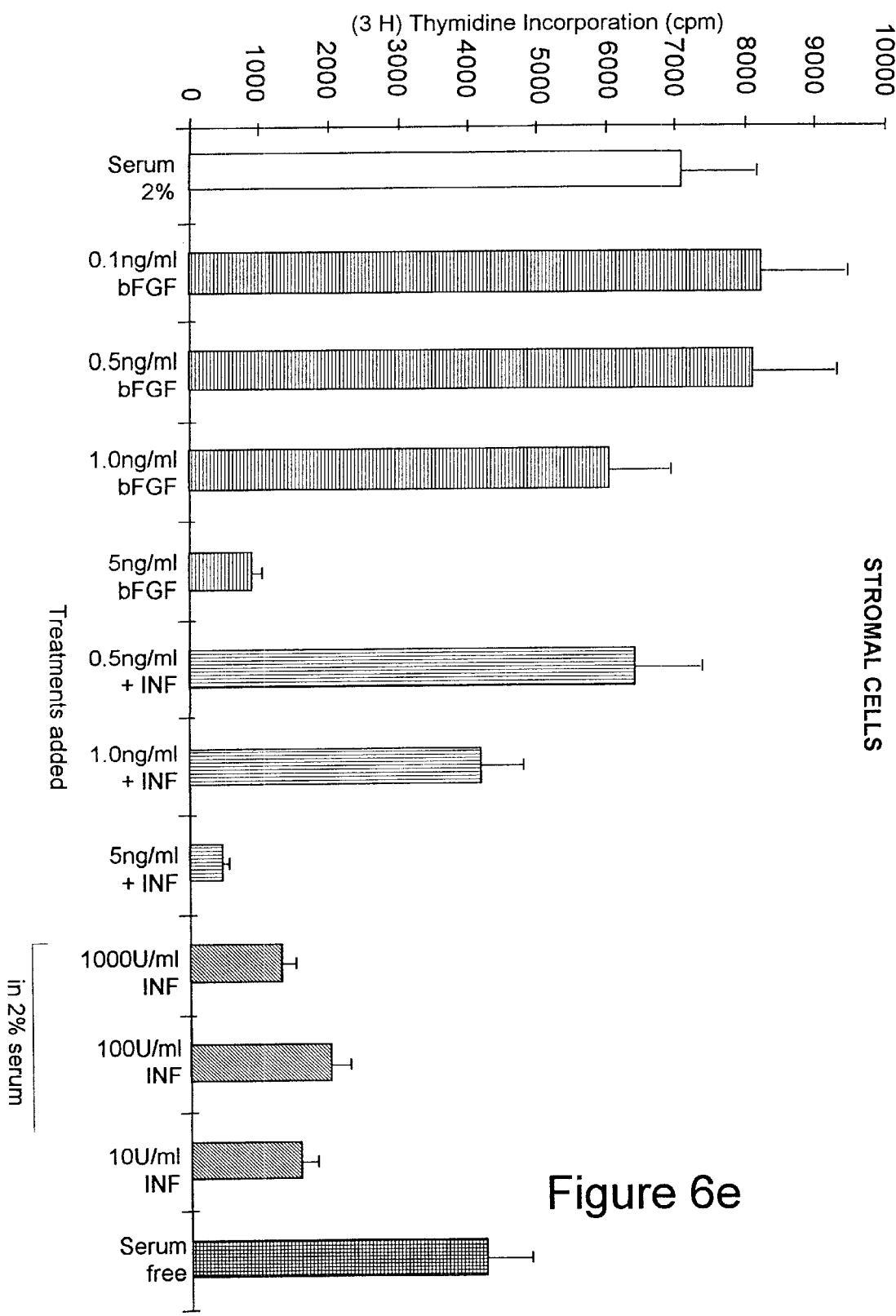
FIG. 6e shows the effects of interferon-α on DNA synthesis in endometrial stromal cells.

We have carried out similar studies on endometrial stromal cells and the results are shown in FIG. 6e. Interferons blocked both bFGF and serum-stimulated DNA synthesis in these cells. The results show the effects of increasing concentrations of bFGF on DNA synthesis in the absence and presence of 100 U/ml interferon-$\alpha$. The results also show the effects of increasing concentrations of interferon-alpha on serum stimulated DNA synthesis.

Figure 7:
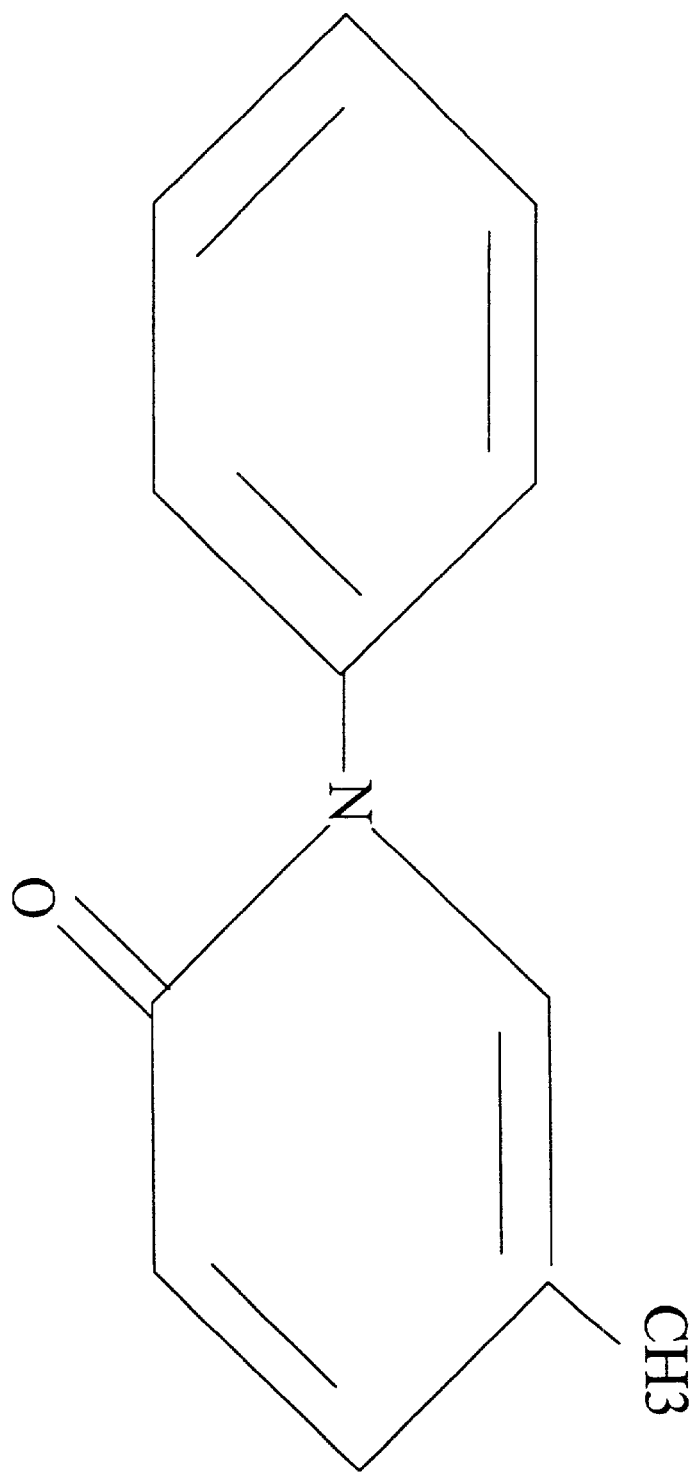
FIG. 7 depicts the chemical structure of pirfenidone.
Figure 8:
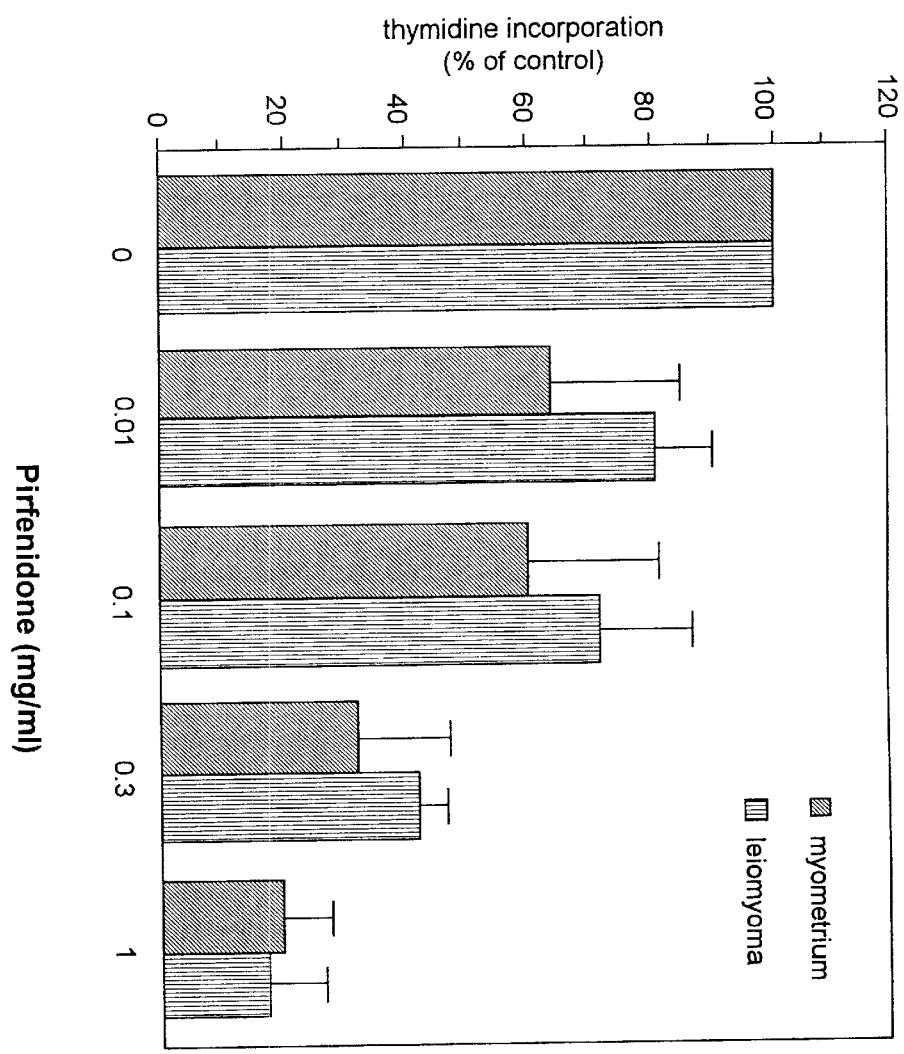
FIG. 8 shows the effects of pirfenidone on myometrial and leiomyoma cell proliferation.
Figure 9A:
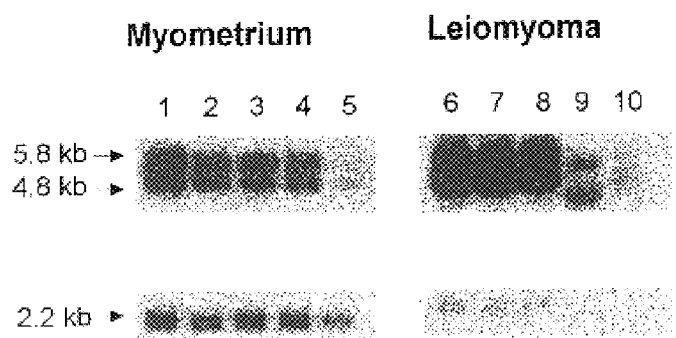
FIG. 9 shows the effects of pirfenidone on collagen type I messenger RNA expression in myometrial and leiomyoma cells.
Figure 9B:
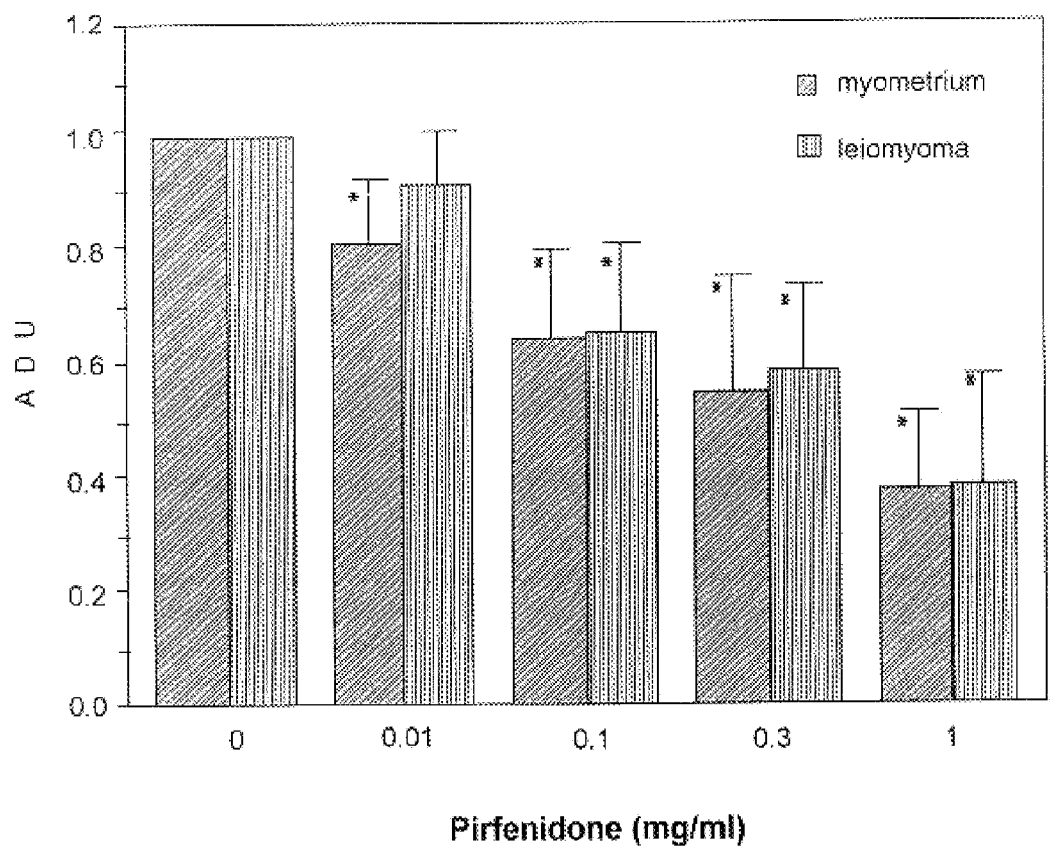
Figure 10A:
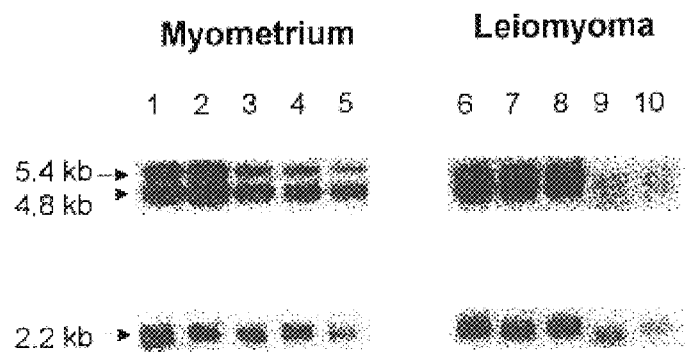
FIG. 10 shows the effect of pirfenidone on collagen type III messenger RNA expression in myometrial and leiomyoma cells.
Figure 10B:
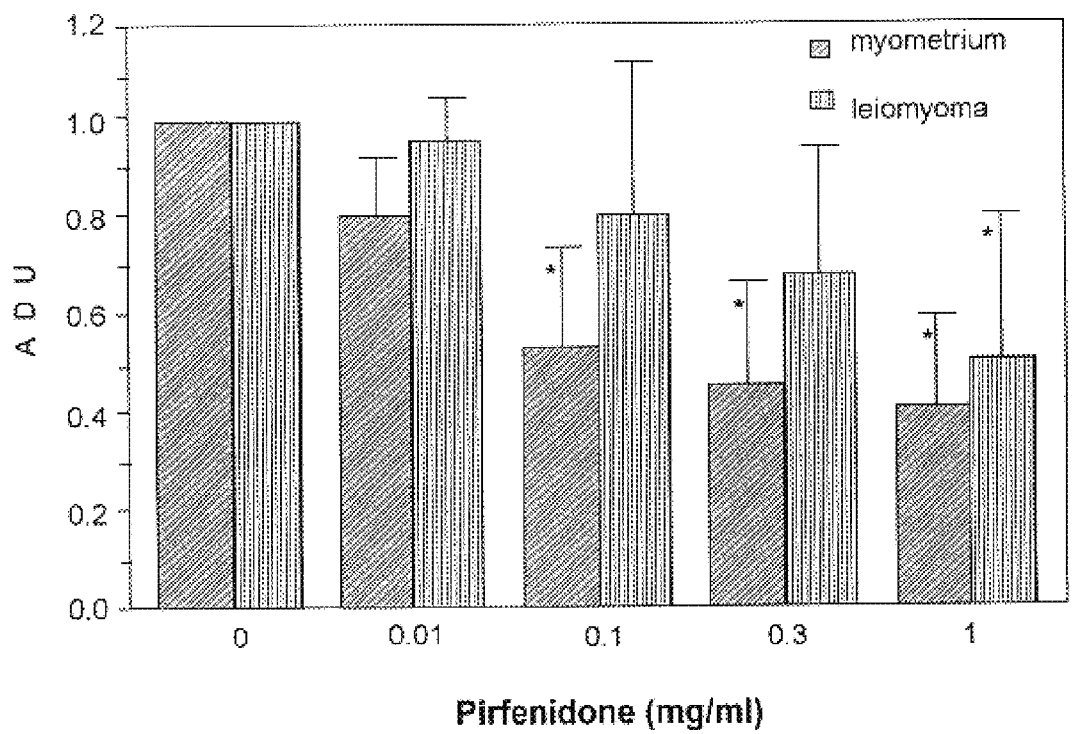

We have also discovered that pirfenidone is a response-blocking compound. Pirfenidone is an antifibrotic agent which is being investigated for use in patients with pulmonary fibrosis. It is an investigational drug whose structure is 5-methyl-1 -phenyl-2-(1H)-pyridone as shown in FIG. 7. Pirfenidone has previously been shown to inhibit fibroblast proliferation in vitro in response to a number of growth factors including basic fibroblast growth factor (bFGF), transforming growth factor beta (TGFB), and platelet derived growth factor (PDGF) (reference: Lurton, J M, Margolin, S B, Raghu G. 1996. Pirfenidone inhibits the stimulatory effects of pro-fibrotic cytokines on human fibroblasts in vitro. Am. J. Respir. Crit. Care Med. 153: A403. The effects of pirfenidone on proliferation of myometrial and leiomyoma cells using tritiated thymidine incorporation assays and by measuring changes in actual cell number are shown in FIG. 8. Possible cytotoxic effects were examined using lactate dehydrogenase assays and trypan blue exclusion. Effects on collagen type I and type III production were assessed by RNA blotting as shown in FIGS. 9 and 10.

These results revealed that pirfenidone inhibited cell proliferation in a dose dependent manner and that there was no cytotoxic effect on the cells at the doses tested. Pirfenidone also reduced the levels of RNA for both collagen type I and type III in both cell types. Additionally, as shown in FIG. 11, the effect of pirfenidone treatment on lactate dehydrogenase (LDH) production by myometrial and leiomyoma cells was examined. No significant effects of pirfenidone on LDH levels was observed, however. Additionally, the effect of pirfenidone on cell proliferation and the percentage of dead cells was examined, and the results from the two experiments are shown in FIG. 12. Pirfenidone caused a dose dependent inhibition of cell proliferation for both leiomyoma and myometrial cells ($p<0.01$). A significant increase in the percentage of dead cells was apparent only at 1.0 mg/ml pirfenidone ($p<0.05$).

In addition, we have discovered that heparin, heparin-like polyaromatic anionic compounds, heparin-sulfate-based compounds, secreted or soluble FGF receptors, and/or RGD-peptide control abnormal uterine bleeding by blocking uterine stromal cell response to is angiogenic growth factors.

In this regard it will be appreciated methods and compounds according to the invention control uterine bleeding by targeting the uterine cells, since they express fibroblast growth factor receptors and respond to FGF with an increase in proliferation. In order for the FGFs to bind to and activate their specific cellular receptors they need to also interact with compounds called heparin-sulfate proteoglycans. It is understood that the physical binding of FGF to the heparin-sulfate somehow confers the correct conformation on the FGF molecule so that it can bind to its specific cell surface receptor. The compound suramin, which is a polysulfonic naphthalene antihelminthic drug, has been shown to interfere with the ability of FGFs to bind to their specific cell surface receptors. This compound binds close to the receptor-binding domain of basic FGF, inducing local conformational changes, which prevent FGF from binding to the specific cell surface receptor. Suramin essentially takes the place of the heparin sulfate (ie, it binds to the FGF molecule, but it inhibits rather than promotes binding to the cell surface receptor).

Thus, suramin is also a very potent inhibitor of FGF induced proliferation in a wide variety of cells, including vascular smooth muscle cells, T cells, and fibroblasts, and the present invention contemplates the use of sumarin as growth receptor blocker. (References; 1. Ranson M R, Stone A L, Chen R, Porter D, and Myers C E. (1993). Molecular mechanism for the regulation of fibroblast growth factor by the polyanions heparin and suramin. British J Cancer 67:11. 2. Stein C A, LaRocca R V, Thomas R, McAtee N, Myers C E. (1989). Suramin: an anticancer drug with a unique mechanism of action. J Clin Oncol 7:499. 3. Mills G V, Zhang N, May C, Hill M, Chung A. (1990). Suramin prevents binding of interleukin 2 to its cell surface receptor: a possible mechanism for immunosuppression. Cancer Res 50:3036.

Other examples of receptor blockers include the two secreted forms of the FGF receptor by uterine cells (binding proteins) which have been identified will be useful inhibitors of the binding of bFGF to its cell surface receptors. These soluble (secreted) forms of the FGF receptor have been identified in blood and vitreous fluid (References: Hanneken, Ying, Ling, Baird, (1994) Proc. Natl. Acad. Sci. 91:9170; Hanneken and Baird, 1995, Invest. Opthalmol. Vis. Sci. 36: 1192. ).

Figure 13A:
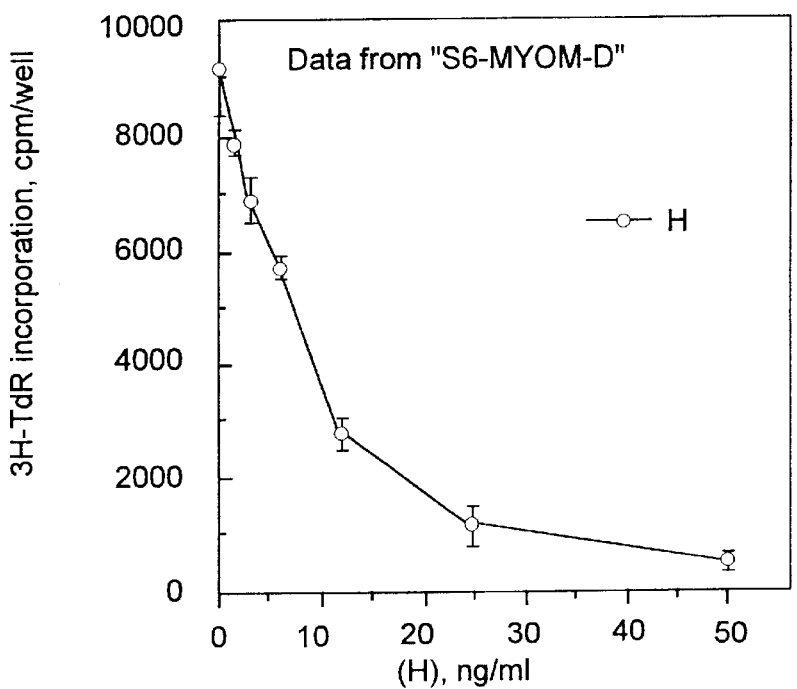
FIG. 13 shows the effect of the heparin-like compounds H (a heparin/heparin-sulfated disaccharide repeating unit of iduronic/glucoronic acid and glucosamine), 16 (a polymer of 2-(4-hydroxyphenoxyacetic acid) and formaldehyde), and PASA (polyanionic sumarin) on the proliferation of myometrial cells.
Figure 13B:
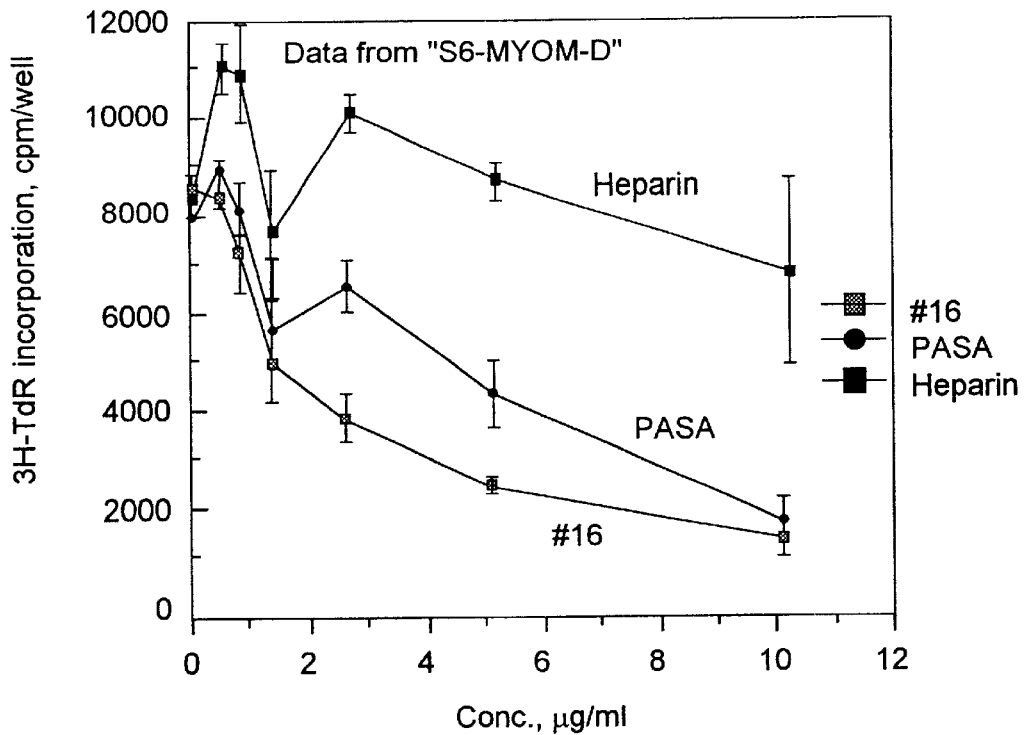
Figure 14A:
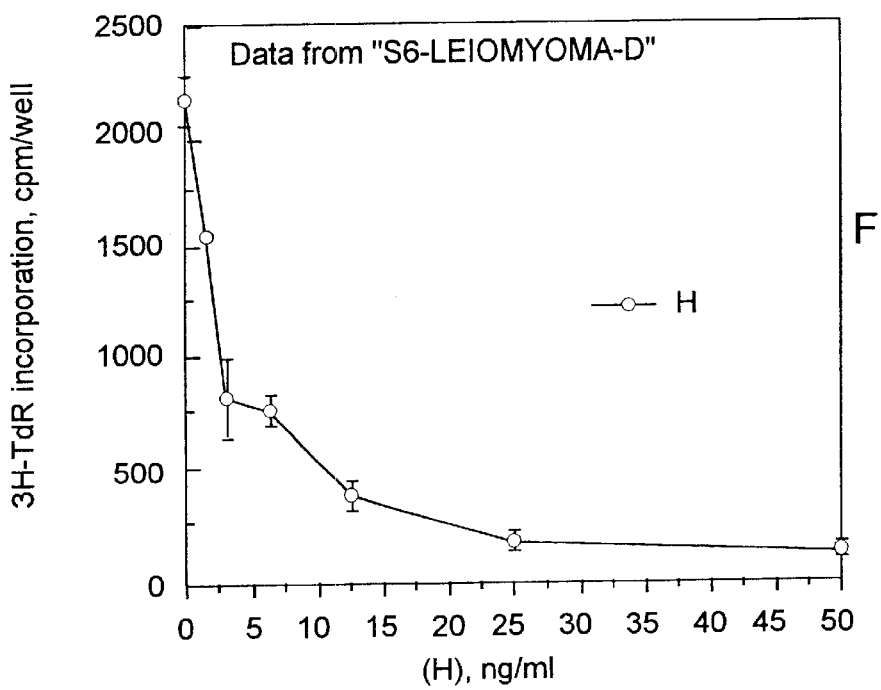
FIG. 14 shows the effect of the heparin-like compounds H (a heparin/heparin-sulfated disaccharide repeating unit of iduronic/glucoronic acid and glucosamine), 16 (a polymer of 2-(4-hydroxyphenoxyacetic acid) and formaldehyde), and PASA (polyanionic sumarin) on the proliferation of leiomyoma cells.
Figure 14B:
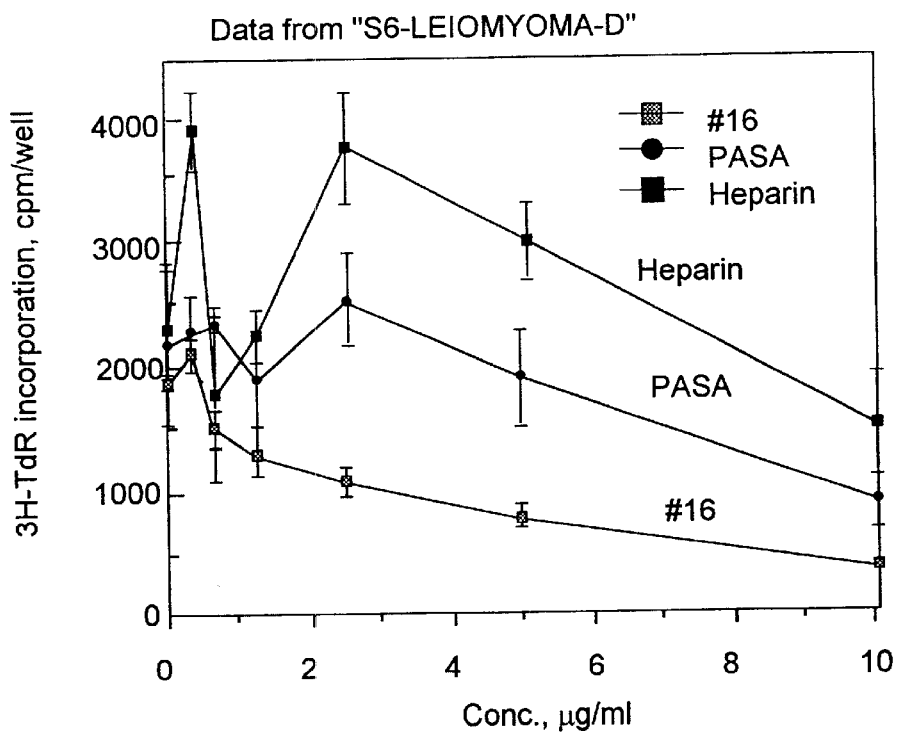

Yet other examples include heparin and heparin-like polyaromatic anionic compounds which also inhibit FGF binding to its specific cell surface receptor by again, competing with the heparin sulfate, and thus by taking the place of the heparin sulfate, preventing the FGF from achieving its correct physical conformation so that it can bind to the specific cell surface receptor. Heparin and heparin-like compounds have been shown to be very good inhibitors of smooth muscle cell proliferation, and certain tumor cells. FIGS. 13 and 14 show the effect of two heparin-like compounds on the proliferation of myometrial and leiomyoma cells. All of these compounds showed a significant suppression of DNA synthesis, and an improved suppression of DNA synthesis relative to heparin. Thus, the present invention contemplates the use of these and related compounds as potential inhibitors of the FGF growth factor. (References: 1. Ranson et al., listed in above paragraph. 2. Benezra M, Ben-Sasson S A, Regan J, Chang M, Bar-Shavit R, Vlodavsky I. (1994). Antiproliferative activity to vascular smooth muscle cells and receptor binding of heparin-mimicking polyaromatic anionic compounds. Arterioscler Thromb 14:1992. 3. Fernig D G, Rudland P S, Smith J A (1992). Rat mammary myoepithelial-like cells in culture possess kinetically distinct low-affinity receptors for fibroblast growth factor that modulate growth stimulatory responses. Growth Factors 7:27

Immunohistochemical Localization of FGFRI in Human Uterine Tissues Throughout the Menstrual Cycle A shown in FIG. 2, panels A, C, E, G are negative controls and were treated with nonspecific IgG at a concentration of 5 ug/ml. Panels B, D, F, H, and J are treated with a mouse monoclonal antibody against FGFR1 at a concentration of 2 ug/ml. All endometrial samples shown are from patients with no abnormal bleeding. Panels A and B show early proliferative endometrium with moderate glandular staining and stromal cells showing significant cytoplasmic staining. Panels C and D show a sample of day 17 endometrium. The glandular staining is similar with no staining of the endometrial stroma. Panels E and F show day 24 endometrium. Significant cytoplasmic staining is seen in the stroma as well as the glandular staining. Panels G and H show day 22 endometrium with part of the underlying myometrium. Discrete staining is seen in the glands with minimal endometrial stromal staining. The myometrial smooth muscle cells show strong staining. Panels I and J show a leiomyoma with light staining throughout the extracellular matrix and some cell associated staining but overall decreased staining when compared to that of normal myometrium.

RT-PCT Detection of FGFR1 Isotypes

As shown in FIG. 3, the three extracellular immunoglobulin-like domains (Ig) are diagrammed leading to the transmembrane portion of the molecule (A). Primers are indicated with capital letters for ease of reference and fragments are diagrammed in portion and with relative sizes represented. The sequence of downstream primer C is repeated in both of the first two immunoglobulin domains (Ig I and Ig II) and thus led to amplification of secreted form A in addition to the anticipated fragments. (B) shows the amplification of the complete and alternatively spliced transmembrane forms of the FGFR1 from human endometrium.

The molecular weight standards are seen in lane 1. Lane 2 shows a 315 bp product representing the complete form, lane 3 represents 540, 432 and 165 bp products. The 432 and 165 bp products are consistent with both the complete and alternatively spliced transmembrane forms, respectively. The 540 bp product was sequenced and identified as a secreted form B. Lane 5 shows a sample that did not receive reverse transcriptase and thus serves as a negative control. Identical results were seen from 8 other endometrial specimens and similar numbers of leiomyoma and myometrial samples. (C) depicts restriction digests for both the complete and alternatively spliced forms of the receptor. Lane 1 is the molecular weight standard. Lanes 2, 3 and 4 represent Ava II digestions of amplified samples from amplification of endometrium, myometrium and leiomyoma, respectively from a single patient. Both the 183 and the 132 bp fragment are seen in all lanes. Lanes 5, 6 and 7 show HinfI digestion of the same samples to identify the alternatively spliced form. The 130 bp fragment is seen in all lanes and the 35 bp fragment is unable to be visualized due to its small size. Identical results were seen for 7 other triplicate samples and leiomyoma/myometrium pairs for normal women. D shows the restriction digestion of the amplified secreted FGFR1 from B utilizing AvaII and shows both the 219 and the 122 bp product for leoiomyomas (lane 2), myometrium (lane 3) and endometrium (lane 4) from a single patient. Molecular weight markers are seen in lane 1. Identical results were seen in tissue samples from 8 other patients and myometrial and endometrial samples obtained from normal women.

Protein Immunoblot Identifying the Two Secreted Forms of the Receptor

In FIG. 4, the protein immunoblot identifying the two secreted forms of the receptor is shown. Lane 1 (St) shows protein molecular weight standards. Lanes 2 (E), 3 (L) and 4 (M) show proteins obtained from endometrium, leiomyomas and myometrium from a single patient. The two proteins of 69,000 and 61,000 MW represent two different secreted forms of the type 1 FGF receptor. All 4 proteins were detected equally in each tissue type although due to the efficiency of protein detection, 4 bands were not detected for each sample. A representative gel of the 5 gels run is shown with all 4 bands seen for leiomyoma and 3 of the 4 bands visualized for myometrium and endometrium.

Stimulation of the Proliferation of Uterine Stromal Cells

Stromal cells were used at the first passage and were plated into 100 mm dishes (200,000/dish) in serum-containing medium. The following day, cells were rinsed and transferred to serum-free medium containing insulin, transferrin and selenium. Cells remained in this medium for 48 hr to induce quiescence and then received fresh serum-free medium with one of the following treatments: ITS (medium containing only insulin, transferin, and selenium), ITS+10% fetal bovine serum, MPA (ITS+100 nm medroxy progesterone acetate), E2 (ITS+10 nm estradiol 17-beta), bFGF (ITS+10 ng/ml bFGF), bFGF/E2/MPA (ITS+100 nm MPA+10 nm estradiol+10 ng/ml bFGF), bFGF+2% fetal bovine serum (ITS+10 ng/ml bFGF+2% fetal bovine serum), bFGF+MPA (ITS+10 ng/ml bFGF+100 nm MPA) and bFGF+E2 (TS+10 ng/ml bFGF+10 nm estradiol). Cells were treated for a total of 7 days with cell counts performed on days 2, 4 and 7. As shown in FIGS. 5*a* and 5*b,* stromal cells showed an increase in cell proliferation only in the presence of bFGF and progesterone.

Effects of Interferon-α

Myometrial and leiomyoma cells from the same patients were used at first passage for proliferation assays. 10,000 cells were plated per well in 96-well plates in medium+10 % serum. Cells were cultured for three days and then placed in serum-free medium for 48 hr to attain quiescence. Interferon-α was tested at the following doses in 10% serum-containing medium; 0, 10, 100 and 1000 U/ml for a period of 24 hr. Tritiated thymidine (luCi/ml) was added to the culture wells for the final 4–6 hr of incubation, the medium removed, cells harvested and counted for thymidine incorporation.

As shown in FIGS. 6*a* and 6*b,* interferon-α was tested at three concentrations-10 U/ml, 100 U/ml and 1000 U/ml. Effects on basal DNA synthesis were tested using cells cultured in serum-free medium containing only 0.1% BSA while effects on serum-stimulated cells were assessed using cells cultured in medium with 10% fetal bovine serum.

FIGS. 6*c* and 6*d* show the effects of interferon-α on bFGF induced increases in DNA synthesis by uterine myometrial and leiomyoma cells, respectively. Cells were treated with either medium+10% serum of various concentrations of bFGF (0.5 ng/ml, 1.0 ng/ml, 5.0 ng/m. and 10 ng/ml) to compare mitogenic effects. Cells cultured in serum were also treated with interferon-α at 10, 100 and 1000 U/ml, while cells cultured in the various concentrations of bFGF were treated with 100 U/ml of interferon α.

FIG. 6*e* shows the effect of interferon-α on bFGF induced increases in DNA synthesis by endometrial stromal cells. The results show the effects of increasing concentrations of bFGF (0.1 ng/ml, 0.5 ng/ml, 1.0 ng/ml and 5 ng/ml) on DNA synthesis in the absence and presence of 100 U/ml interferon-alpha. The results also show the effects of increasing concentrations of interferon-alpha (10, 100 and 1000 U/ml) on serum (2%) stimulated DNA synthesis.

Described above are methods, compounds and devices meeting the objects set forth above. It should be understood that various changes and modifications of the preferred embodiments may be made within the scope of the invention. Thus, for example, whereas the discussion above focuses on use of interferons, heparin, heparin-like polyaromatic anionic compounds, heparin-sulfate-based compounds, secreted or soluble FGF receptors, and/or RGD-peptide to block response by uterine stromal cells to angiogenic growth factors as specific examples, other compounds not listed here may well provide equivalent such actions for the presently claimed invention.

What is claimed is:

1. A method for treating abnormal uterine bleeding comprising administering to a patient a response-blocking compound that blocks uterine stromal cell response to angiogenic growth factors.

2. The method of claim 1, wherein the response-blocking compound blocks uterine stromal cell response to any of basic fibroblast growth factor (bFGF), FGF receptor (FGFR), acidic fibroblast growth factor (aFGF), transforming growth factor β (TGF-β), platelet-derived growth factor (PDGF), heparin binding epidermal growth factor (HBEGF), vascular endothelial growth factor (VEGF), parathyroid hormone-related protein (PTHrP) and prolactin.

3. The method of claim 2, wherein the response-blocking compound inhibits expression of and response to bFGF, FGFR, aFGF, TGF-β, PDGF, HBEGF, VEGF, PTHrP, or prolactin by the uterine stromal cells.

4. The method of claim 1, wherein the response-blocking compound includes one or more of interferons, pirfenidone, heparin, heparin-like polyaromatic anionic compounds, heparin-sulfate-based compounds, secreted or soluble FGF receptors, and RGD-peptide.

5. The method of claim 4, wherein the response-blocking compound includes a type I interferon.

6. The method of claim 5, wherein the response-blocking compound is administered systemically to the patient or locally to the uterus.

7. The method of claim 6, wherein the response-blocking compound is administered such that dosages in the range of 1 to 10,000 U/ml thereof are present in any bodily tissues or fluids surrounding the uterine stromal cells.

8. The method of claim 7, wherein the response-blocking compound is administered such that dosages in the range of 100 to 1000 U/ml thereof are present in any bodily tissues fluids surrounding the uterine stromal cells.

9. The method of claim 8, wherein the response-blocking compound is administered for a period of 1 to 30 days.

10. The method of claim 9, wherein the response-blocking compound is administered for a period of 3 to 10 days.

11. The method of claim 5, wherein the response-blocking compound is administered to the patient by any of ingestion, subcutaneous injection, intramuscular injection, subcutaneous implantation, suppository, cream, foam, capsule, and cavity implant.

12. A device for treatment of abnormal uterine bleeding comprising any of a subcutaneous, uterine and vaginal implant for delivery of a response-blocking compound that blocks uterine stromal cell response to angiogenic growth factors.

13. The device of claim 12, wherein the implant delivers a response-blocking compound that blocks uterine stromal cell response to any of basic fibroblast growth factor (bFGF), FGF receptors (FGFR), acidic fibroblast growth factor (aFGF), transforming growth factor β (TGF-β), platelet-derived growth factor (PDGF), heparin binding epidermal growth factor (HBEGF), vascular endothelial growth factor (VEGF), parathyroid hormone-related protein (PTHrP) and prolactin.

14. The device of claim 13, wherein the implant delivers a response-blocking compound that inhibits any of expression of and response to any of bFGF, FGFR, aFGF, TGF-β, PDGF, HBEGF, VEGF, PTHrP, and prolactin by the uterine stromal cells.

15. The device of claim 12, wherein the implant delivers a response-blocking compound including one or more of an interferon, pirfenidone, heparin, heparin-like polyaromatic anionic compounds, heparin-sulfate-based compounds, secreted or soluble FGF receptors, and RGD-peptide.

16. The device of claim 15, wherein the response-blocking compound includes a type I interferon.

17. The device of claim 12, wherein the implant delivers the response-blocking compound to the patients such that dosages in the range of 1 to 10,000 U/ml thereof are present in any bodily tissues or fluids surrounding the uterine stromal cells.

18. The device of claim 17, wherein the implant delivers the response-blocking compound to the patients such that dosages in the range of 100 to 1000 U/ml thereof are present in any bodily tissues or fluids surrounding the uterine stromal cells.

19. The device of claim 18, wherein the implant delivers the response-blocking compound for a period of 1 to 30 days.

20. The device of claim 19, wherein the implant delivers the response-blocking compound for a period of 3 to 10 days.

21. A method for female contraception comprising administering to a patient (i) a progestin-based contraceptive, and (ii) a response-blocking compound that blocks uterine stromal cell response to angiogenic growth factors.

22. The method of claim 1, wherein the response-blocking compound blocks uterine stromal cell response to any of basic fibroblast growth factor (bFGF), FGF receptors (FGFR), acidic fibroblast growth factor (aFGF), transforming growth factor β (TGF-β), platelet-derived growth factor (PDGF), heparin binding epidermal growth factor (HBEGF), vascular endothelial growth factor (VEGF), parathyroid hormone-related protein (PTHrP) and prolactin.

23. The method of claim 22, wherein the response-blocking compound inhibits any of expression of and response to any of bFGF, FGFR, aFGF, TGF-β, PDGF, HBEGF, VEGF, PTHrP, and prolactin by the uterine stromal cells.

24. The method of claim 21, wherein the response-blocking compound includes one or more of interferons, pirfenidone, heparin, heparin-like polyaromatic anionic compounds, heparin-sulfate-based compounds, secreted or soluble FGF receptors, and RGD-peptide.

25. The method of claim 24, wherein the response-blocking compound includes a type I interferon.

26. The method of claim 25, wherein the response-blocking compound and the progestin-based contraceptive are administered systemically to the patient and locally to the uterus.

27. The method of claim 26, wherein the response-blocking compound is administered such that dosages in the range of 1 to 10,000 U/ml thereof are present in any bodily tissues or fluids surrounding the uterine stromal cells.

28. The method of claim 27, wherein the response-blocking compound is administered such that dosages in the range of 100 to 1000 U/ml thereof are present in any bodily tissues or fluids surrounding the uterine stromal cells.

29. The method of claim 28, wherein the response-blocking compound is administered for a period of 1 to 30 days.

30. The method of claim 29, wherein the response-blocking compound is administered for a period of 3 to 10 days.

31. The method of claim 21, wherein the response-blocking compound and progestin-based contraceptive are administered to the patient by any of ingestion, subcutaneous injection, intramuscular injection, subcutaneous implantation, suppository, cream, foam, capsule, and cavity implant.

32. A device for female contraception, comprising any of a subcutaneous, uterine and vaginal implant for delivery of a progestin-based contraceptive and a response-blocking compound that blocks uterine stromal cell response to angiogenic growth factors.

33. The device of claim 32, wherein the implant delivers a response-blocking compound that blocks uterine stromal cell response to any of basic fibroblast growth factor (bFGF), FGF receptors (FGFR), acidic fibroblast growth factor (aFGF), transforming growth factor β (TGF-β), platelet-derived growth factor (PDGF), heparin binding epidermal growth factor (HBEGF), vascular endothelial growth factor (VEGF), parathyroid hormone-related protein (PTHrP) and prolactin.

34. The device of claim 33, wherein the implant delivers a response-blocking compound that inhibits any of expression of and response to any of bFGF, FGFR, aFGF, TGF-β, PDGF, HBEGF, VEGF, PTHrP, and prolactin by the uterine stromal cells.

35. The device of claim 32, wherein the implant delivers a response-blocking compound including one or more of an interferon, pirfenidone, heparin, heparin-like polyaromatic anionic compounds, heparin-sulfate-based compounds, secreted or soluble FGF receptors, and RGD-peptide.

36. The device of claim 35, wherein the response-blocking compound includes a type I interferon.

37. The device of claim 32, wherein the implant delivers the response-blocking compound to the patients such that dosages in the range of 1 to 10,000 U/ml thereof are present in any bodily tissues or fluids surrounding the uterine stromal cells.

38. The device of claim 37, wherein the implant delivers the response-blocking compound to the patients such that dosages in the range of 100 to 1000 U/ml thereof are present in any bodily tissues or fluids surrounding the uterine stromal cells.

39. The device of claim 38, wherein the implant delivers the response-blocking compound for a period of 1 to 30 days.

40. The device of claim 39, wherein the implant delivers the response-blocking compound for a period of 3 to 10 days.

41. A compound for female contraception, comprising a progestin-based contraceptive and a response-blocking compound that blocks uterine stromal cell response to angiogenic growth factors.

42. The compound of claim 41, the response-blocking compound blocks uterine stromal cell response to any of basic fibroblast growth factor (bFGF), FGF receptors (FGFR), acidic fibroblast growth factor (aFGF), transforming growth factor $\beta$ (TGF-$\beta$), platelet-derived growth factor (PDGF), heparin binding epidermal growth factor (HBEGF), vascular endothelial growth factor (VEGF), parathyroid hormone-related protein (PTHrP) and prolactin.

43. The compound of claim 42, wherein the response-blocking compound inhibits any of expression of and response to any of bFGF, FGFR, aFGF, TGF-$\beta$, PDGF, HBEGF, VEGF, PTHrP, and prolactin by the uterine stromal cells.

44. The compound of claim 43, wherein the response-blocking compound including one or more of an interferon, pirfenidone, heparin, heparin-like polyaromatic anionic compounds, heparin-sulfate-based compounds, secreted or soluble FGF receptors, and RGD-peptide.

45. The compound of claim 44, wherein the response-blocking compound includes a type I interferon.

46. A method for determining a non-pregnant female patient's propensity for abnormal uterine bleeding, comprising the steps of:
   A. applying a labelled angiogenic growth factor receptor to a biological sample obtained from the non-pregnant patient,
   B. determining an affinity of the labelled angiogenic growth factor to the sample,
   C. comparing that affinity with an affinity of the labelled angiogenic growth factor to biological samples from (i) a population of non-pregnant women that experience abnormal uterine bleeding and (ii) a population of non-pregnant women that do not experience abnormal uterine bleeding.

* * * * *

UNITED STATES PATENT AND TRADEMARK OFFICE
CERTIFICATE OF CORRECTION

PATENT NO.    : 6,440,445 B1
DATED         : August 27, 2002
INVENTOR(S)   : Nowak et al.

It is certified that error appears in the above-identified patent and that said Letters Patent is hereby corrected as shown below:

Column 14,
Line 58, please delete "and" insert therefore -- or --.

Column 15,
Lines 6, 9, 49 and 54, please delete "any".

Column 16,
Line 26, please delete "and"; and insert therefore -- or --;
Lines 24 and 28, please delete "any".

Column 17,
Lines 4 and 9, please delete "any".

Signed and Sealed this

Eighth Day of July, 2003

JAMES E. ROGAN
*Director of the United States Patent and Trademark Office*